(12) United States Patent
Todd et al.

(10) Patent No.: US 8,137,407 B2
(45) Date of Patent: Mar. 20, 2012

(54) TIBIAL KNEE COMPONENT WITH A MOBILE BEARING

(75) Inventors: Dwight T. Todd, Columbia City, IN (US); Brian D. Byrd, North Webster, IN (US); James C. Harris, Warsaw, IN (US); Kim C. Bertin, Salt Lake City, UT (US); Linggawati Tanamal, Singapore (SG); Peter S. Walker, New York, NY (US)

(73) Assignee: Zimmer, Inc., Warsaw, IN (US)

( * ) Notice: Subject to any disclaimer, the term of this patent is extended or adjusted under 35 U.S.C. 154(b) by 704 days.

(21) Appl. No.: 11/075,464

(22) Filed: Mar. 9, 2005

(65) Prior Publication Data

US 2005/0209702 A1 Sep. 22, 2005

Related U.S. Application Data

(60) Provisional application No. 60/552,104, filed on Mar. 9, 2004.

(51) Int. Cl.
*A61F 2/38* (2006.01)
(52) U.S. Cl. .................. 623/20.33; 623/20.15
(58) Field of Classification Search .............. 623/20.26, 623/20.28, 20.33, 20.32, 20.15
See application file for complete search history.

(56) References Cited

U.S. PATENT DOCUMENTS

| | | | |
|---|---|---|---|
| 4,309,778 A | 1/1982 | Buechel | |
| 4,728,332 A | 3/1988 | Albrektsson | |
| 4,936,853 A | 6/1990 | Fabian | |
| 5,047,057 A | 9/1991 | Lawes | |
| 5,071,438 A | 12/1991 | Jones | |
| 5,282,868 A | 2/1994 | Bahler | |
| 5,336,266 A | 8/1994 | Caspari | |
| 5,370,699 A | 12/1994 | Hood | |
| 5,395,401 A | 3/1995 | Bahler | |

(Continued)

FOREIGN PATENT DOCUMENTS

DE 101 20 162 C1 7/2002

(Continued)

OTHER PUBLICATIONS

Callaghan, et al., Mobile-Bearing Knee Replacement, The Journal of Bone and Joint Surgery, vol. 82-A, No. 7, Jul. 2000, pp. 1020-1041.

(Continued)

*Primary Examiner* — Thomas J Sweet
*Assistant Examiner* — Melissa Hoban
(74) *Attorney, Agent, or Firm* — Faegre Baker Daniels LLP

(57) ABSTRACT

A mobile bearing knee prosthesis apparatus includes a tibial plate. The tibial plate includes a medial lobe and a lateral lobe conjoined in a dividing plane. The apparatus further includes a tibio-femoral insert and a stud-like protuberance extending from the tibial plate into the tibio-femoral insert. The stud-like protuberance includes a protuberance sidewall positioned in the tibio-femoral insert. The protuberance sidewall is bisected by the dividing plane and includes a pair of opposing eccentric convex arcuate portions, and the tibio-femoral insert is moveable relative to the tibial plate about an axis medially disposed from the dividing plane. A mobile bearing knee prosthesis apparatus includes a tibial plate and a tibio-femoral insert coupled to the tibial plate. The tibio-femoral insert includes a generally posteriorly positioned chamfered superior surface and defines a generally posteriorly positioned generally U-shaped space bounded at least in part by the chamfered surface.

24 Claims, 25 Drawing Sheets

U.S. PATENT DOCUMENTS

| | | | | |
|---|---|---|---|---|
| 5,413,604 A * | 5/1995 | Hodge | | 623/20.28 |
| 5,413,608 A | 5/1995 | Keller | | |
| 5,609,639 A | 3/1997 | Walker | | |
| 5,613,970 A | 3/1997 | Houston | | |
| 5,658,342 A | 8/1997 | Draganich | | |
| 5,683,468 A | 11/1997 | Pappas | | |
| 5,702,463 A | 12/1997 | Pothier | | |
| 5,702,466 A | 12/1997 | Pappas | | |
| 5,755,801 A * | 5/1998 | Walker et al. | | 623/20.21 |
| 5,782,920 A | 7/1998 | Colleran | | |
| 5,782,925 A * | 7/1998 | Collazo et al. | | 623/20.28 |
| 5,871,541 A | 2/1999 | Gerber | | |
| 5,871,542 A | 2/1999 | Goodfellow | | |
| 5,871,543 A | 2/1999 | Hofman | | |
| 5,871,545 A * | 2/1999 | Goodfellow et al. | | 623/20.28 |
| 5,879,392 A * | 3/1999 | McMinn | | 623/20.28 |
| 5,879,394 A | 3/1999 | Ashby | | |
| 5,906,643 A | 5/1999 | Walker | | |
| 5,928,286 A * | 7/1999 | Ashby et al. | | 623/20.33 |
| 6,039,764 A | 3/2000 | Pottenger | | |
| 6,053,945 A * | 4/2000 | O'Neil et al. | | 623/20.32 |
| 6,068,658 A | 5/2000 | Insall | | |
| 6,090,144 A * | 7/2000 | Letot et al. | | 623/20.34 |
| 6,102,954 A | 8/2000 | Albrektsson | | |
| 6,296,666 B1 * | 10/2001 | Gardner | | 623/20.29 |
| 6,299,646 B1 * | 10/2001 | Chambat et al. | | 623/20.33 |
| 6,319,283 B1 * | 11/2001 | Insall et al. | | 623/20.33 |
| 6,413,279 B1 * | 7/2002 | Metzger et al. | | 623/20.29 |
| 6,419,707 B1 * | 7/2002 | Leclercq | | 623/20.33 |
| 6,428,577 B1 * | 8/2002 | Evans et al. | | 623/20.29 |
| 6,554,866 B1 | 4/2003 | Aicher et al. | | |
| 2001/0047211 A1 * | 11/2001 | Leclercq et al. | | 623/20.32 |
| 2005/0021147 A1 | 1/2005 | Tarabichi | | |
| 2006/0036329 A1 | 2/2006 | Webster et al. | | |

FOREIGN PATENT DOCUMENTS

| | | | |
|---|---|---|---|
| DE | 10120162 C1 | | 7/2002 |
| EP | 0336774 A1 | | 10/1989 |
| EP | 0546726 A1 * | | 6/1993 |
| EP | 0634155 A | | 1/1995 |
| EP | 0634155 A2 | | 1/1995 |
| EP | 0634155 A2 * | | 1/1995 |
| EP | 0634156 A | | 1/1995 |
| EP | 0634156 A2 | | 1/1995 |
| EP | 0809987 A2 | | 12/1997 |
| EP | 1064889 A | | 1/2001 |
| EP | 1064889 A2 | | 1/2001 |
| EP | 1097679 A1 | | 5/2001 |
| EP | 1136045 A2 | | 9/2001 |
| FR | 2 830 435 A | | 4/2003 |
| FR | 2830435 A1 * | | 4/2003 |
| GB | 2280375 A | | 2/1995 |
| GB | 2280376 A | | 2/1995 |
| WO | WO93/22990 A1 | | 11/1993 |
| WO | WO9638103 A1 | | 12/1996 |
| WO | WO9730664 A1 | | 8/1997 |

OTHER PUBLICATIONS

Vertullo, et al., Mobile Bearings in Primary Knee Arthroplasty, Journal of the American Academy of Orthopaedic Surgeons, vol. 9, No. 6, Nov./Dec. 2001, pp. 355-364.

Price, et al., A mobile-bearing total knee prosthesis compared with a fixed-bearing prosthesis, The Journal of Bone and Joint Surgery, vol. 85-B, No. 1, Jan. 2003, pp. 62-67.

Kim, et al., Comparison of Fixed-Bearing and Mobile-Bearing Total Knee Arthroplasties, Clinical Orthopaedics and Related Research, No. 392, Nov. 2001, pp. 101-115.

Hollister, et al., The Axes of Rotation of the Knee, Clinical Orthopaedics and Related Research, No. 290, May 1993, pp. 259-268.

Churchill et al., The Transepicondylar Axis Approximates the Optimal Flexion Axis of the Knee, Clinical Orthopaedics and Related Research, No. 356, Nov. 1998, pp. 111-118.

Todo, et al., Anteroposterior and Rotational Movement of Femur During Knee Flexion, Clinical Orthopaedics and Related Research, No. 362, May 1999, pp. 162-170.

Aglietti, et al., Disorders of the Patellofemoral Joint, Surgery of the Knee edited by John N. Insall and W. Norman Scott, Chapter 46, 3d Edition 2001, pp. 913-918.

Aglietti, et al., A New Patella Prosthesis: Design and Application, Clinical Orthopaedics and Related Research, No. 107, Mar.-Apr. 1975, pp. 175-187.

Fox, et al., The Patellofemoral Joint, Chapter 3, 1993pp. 53 and 57.

Yoshioka, et al., Tibial Anatomy and Functional Axes, Journal of Orthopaedic Research, vol. 7, No. 1, 1989, pp. 132-137.

The European Search Report dated Jun. 20, 2005 from the related European Application No. 05005021.0.

The European Search Report dated Sep. 20, 2005 from the related European Application No. 05005021.0.

Office Action mailed Aug. 14, 2007 in the related European Application No. 05005021.0.

Office Action mailed Jul. 30, 2009 in the related European Application No. 05005021.0.

* cited by examiner

TIBIAL KNEE COMPONENT WITH A MOBILE BEARING

CROSS-REFERENCE TO RELATED APPLICATION(S)

This application claims the benefit of U.S. Provisional Patent Application Ser. No. 60/552,104, filed Mar. 9, 2004, entitled "MEDIAL AXIS MOBILE BEARING KNEE PROSTHESIS," which is expressly incorporated herein by reference.

FIELD OF THE INVENTION

The present invention relates generally to the field of orthopaedics, and, more particularly, to a mobile bearing knee prosthesis apparatus.

BACKGROUND

Total joint arthroplasty ("joint replacement") is the surgical replacement of a joint with a prosthesis. A typical knee prosthesis has three main components: a femoral implant, a tibial implant, and a tibio-femoral insert. In general, the femoral implant is designed to replace the distal femoral condyles. The femoral implant is typically made from metal. It typically includes a generally concave, facetted (i.e., piecewise planar) inwardly facing surface defining a cavity for receiving a resected distal femur and typically further includes a generally convex outwardly facing surface with medial and lateral rounded portions for emulating the medial and lateral condyles, respectively, and with a valley or depression between the rounded portions for emulating the patella sulcus/trochlear region of the distal femur. In general, the tibial implant is designed to support and align the tibio-femoral insert. The tibial implant is also typically made from metal. It typically includes a substantially planar tray or plate portion ("tibial plate") for supporting the tibio-femoral insert, and an elongated stem extending distally from the tibial plate for anchoring the tibial implant in the metaphysic and/or intramedullary canal of the proximal tibia. In general, the tibio-femoral insert is designed to replace the tibial plateau and the meniscus of the knee. The tibio-femoral insert is typically made of a strong, smooth, low-wearing plastic. It is typically somewhat disk-shaped, and typically includes one or more substantially planar surfaces for bearing on the tibial plate and one or more generally concave surfaces for bearing against the femoral implant. The tibio-femoral insert also typically provides a clearance space ("patellar cutout") for avoiding the natural patella (if saved) or a prosthetic patella (if the natural patella is resurfaced).

In a traditional knee replacement, a surgeon makes an incision spanning the distal femur, the knee, and the proximal tibia; everts (i.e., flips aside) the patella; separates the distal femur and the proximal tibia from surrounding tissues; and then hyperflexes, distally extends, and/or otherwise distracts the proximal tibia from the distal femur to enlarge the operating space. Next, the surgeon uses various resection guides and saws to prepare the proximal tibia and the distal femur for receiving the replacement prosthesis. A resection guide is a specialized jig or template configured to provide a desired cutting angle for a saw blade or other resection tool. After completing the necessary resections, the surgeon may apply cement to the distal femur and/or to the proximal tibia to ultimately help hold the femoral implant and/or tibial implant, respectively, in place. Alternatively, cementless fixation may be desired. Finally, the surgeon secures the tibial implant and the femoral implant to the proximal tibia and the distal femur, respectively, secures the tibio-femoral insert to the tibial implant, returns the patella or resurfaces it with a prosthetic component, and closes the incision.

In a "fixed bearing" knee prosthesis, the tibio-femoral insert is rotationally fixed relative to the tibial plate; whereas, in a "mobile bearing" knee prosthesis the tibio-femoral insert can pivot relative to the tibial plate to allow proper alignment with the femoral component, reduce stresses at the bone-prosthesis interface, and promote load sharing with surrounding soft tissues. Historically, the pivotal axis of the tibio-femoral insert in mobile bearing designs has been centered between medial and lateral portions of the tibial plate; the tibio-femoral insert has had symmetrical medial and lateral portions; and the patellar cutout has been centered between the medial and lateral portions of the tibio-femoral insert. However, the natural human knee has a pivotal axis that is actually medially offset (i.e., extends only into the medial compartment of the proximal tibia as opposed to being centered between the medial and lateral compartments); the anterior-posterior dimension of the lateral compartment of the natural tibial plateau is actually smaller than that of the medial compartment. Additionally, the risk of bearing dislocation or "spinout" may be undesirably high for some mobile bearing designs that do not incorporate stops to limit the rotation of the tibio-femoral insert; and the posterior cruciate ligament ("PCL"), when saved, may be undesirably impinged by posterior surfaces of some mobile bearing designs.

Moreover, minimally invasive surgical techniques are becoming increasingly popular. Minimally invasive surgeries generally involve, among other things, considerably smaller incisions and tighter working spaces than historical techniques in efforts to reduce patient traumas and accelerate post-operative recoveries. As minimally invasive surgery generally reduces the size of the surgical site, it also generally reduces the amount of space available for inserting, aligning, and securing the prosthetics. Some mobile bearing designs have a tibio-femoral insert that must be installed from above the tibial plate. The substantial exposures and separations of the distal femur and the proximal tibia required for some such "overhead" tibio-femoral insert installations are becoming increasingly incompatible with the space constraints of minimally invasive surgery.

SUMMARY OF THE INVENTION

The present invention provides a mobile bearing knee prosthesis apparatus including a tibial plate. The tibial plate includes a medial lobe and a lateral lobe conjoined in a dividing plane. The apparatus further includes a tibio-femoral insert and a stud-like protuberance extending from the tibial plate into the tibio-femoral insert. The stud-like protuberance includes a protuberance sidewall positioned in the tibio-femoral insert. The protuberance sidewall is bisected by the dividing plane and includes a pair of opposing eccentric convex arcuate portions, and the tibio-femoral insert is moveable relative to the tibial plate about an axis medially disposed from the dividing plane.

The present invention provides a mobile bearing knee prosthesis apparatus including a tibial plate. The tibial plate includes a medial lobe and a lateral lobe conjoined in a dividing plane. The apparatus further includes a tibio-femoral insert and means, integrated with at least one of the tibial plate and the tibio-femoral insert, for moving the tibio-femoral insert relative to the tibial plate about an axis medially disposed from the dividing plane.

The present invention provides a mobile bearing knee prosthesis apparatus including a tibial plate and a tibio-femoral insert coupled to the tibial plate. The tibio-femoral insert includes a generally posteriorly positioned chamfered superior surface and defines a generally posteriorly positioned generally U-shaped space bounded at least in part by the chamfered surface.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

DETAILED DESCRIPTION OF EXEMPLARY EMBODIMENT(S)

Figure 1:
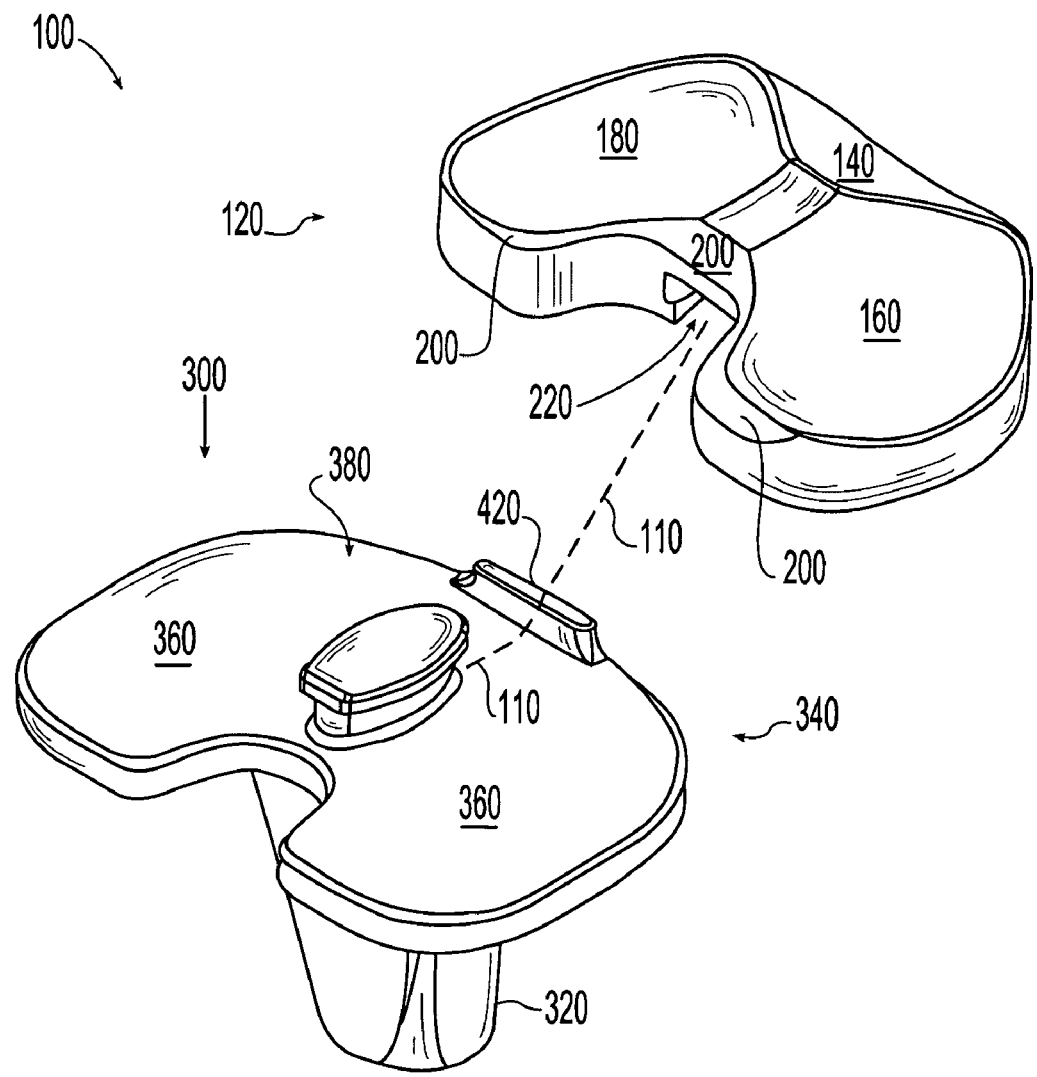
FIG. 1 shows an exploded perspective view of an exemplary mobile bearing knee prosthesis sub-assembly according to the present invention along an explosion/assembly line.

Like reference numerals refer to like parts throughout the following description and the accompanying drawings. As used herein, the terms "medial," "medially," and the like mean pertaining to the middle, in or toward the middle, and/or nearer to the middle of the body when standing upright. Conversely, the terms "lateral," "laterally," and the like are used herein as opposed to medial. For example, the medial side of the knee is the side closest to the other knee and the closest sides of the knees are medially facing, whereas the lateral side of the knee is the outside of the knee and is laterally facing. Further, as used herein the term "superior" means closer to the top of the head and/or farther from the bottom of the feet when standing upright. Conversely, the term "inferior" is used herein as opposed to superior. For example, the heart is superior to the stomach and the superior surface of the tongue rests against the palate, whereas the stomach is inferior to the heart and the palate faces inferiorly toward the tongue. Additionally, as used herein the terms "anterior," "anteriorly," and the like mean nearer the front or facing away from the front of the body when standing upright, as opposed to "posterior," "posteriorly," and the like, which mean nearer the back or facing away from the back of the body.

It is noted, however, that many of the particularly directional and/or positional terms and inflections thereof are used herein merely for clarity of exposition, and at times they may be somewhat arbitrary or interchangeable as known in the art. For example, although the present invention is described herein relative to exemplary left knee embodiments, it should be appreciated that in many cases corresponding right knee embodiments may be made by simply exchanging "medial" and "lateral" indications where appropriate (i.e., medial-lateral mirroring).

FIG. 1 shows an exploded perspective view of an exemplary mobile bearing knee prosthesis sub-assembly 100 according to the present invention along an explosion/assembly line 110. Sub-assembly 100 includes an exemplary tibio-femoral insert 120. Among other things, insert 120 is configured to emulate a natural tibial plateau (not shown) and natural meniscus (not shown) for a left knee replacement. In the exemplary embodiment, insert 120 is made from Ultra High Molecular Weight Polyethylene ("UHMWPE"). In alternative embodiments, insert 120 may be made from any other suitably strong, smooth, low-wearing biocompatible material(s). Insert 120 includes a generally anteriorly positioned generally concave superior surface 140 configured to minimize the possibility of impingement of the natural or prosthetic patella (not shown) and the patellar tendon. Insert 120 also includes a generally medially positioned generally concave superior surface 160 and a generally laterally positioned generally concave superior surface 180 which are configured to bear against a generally symmetrical femoral implant (not shown). In the exemplary embodiment, surface 160 and surface 180 have about the same curvature(s). In alternative embodiments, surface 160 and surface 180 may differ in curvature to accommodate a generally asymmetrical femoral implant (not shown). Insert 120 also includes a generally posteriorly positioned chamfered superior surface 200 configured to minimize soft tissue impingement of a posterior cruciate ligament (not shown). Further, insert 120 defines a generally centrally positioned arcuate cavity or slot 220 that is partially discernable in FIG. 1. Slot 220 is discussed further below.

Sub-assembly 100 further includes an exemplary tibial implant 300. Among other things, implant 300 is configured to anchor into a proximal tibia (not shown) and to support and align insert 120. Implant 300 is medially-laterally symmetrical such that it can be used effectively in either a right or left knee. In the exemplary embodiment, implant 300 is made from a cobalt chrome alloy. In alternative embodiments, implant 300 may be made from a titanium alloy or any other suitable biocompatible material(s). Implant 300 includes a stem 320 configured to anchor into the metaphysic and/or intramedullary canal (not shown) of the proximal tibia (not shown). Implant 300 also includes a tibial plate 340 configured to support and align insert 120. Plate 340 includes a substantially flat highly polished or otherwise suitably smooth superior surface 360. Implant 300 also includes a generally centrally positioned stud-like protuberance 380 extending generally superiorly from plate 340. Among other things, protuberance 380 is configured to cooperate with slot 220 such that insert 120 is moveable relative to plate 340 about a medially-offset axis 400 (see FIG. 2, FIG. 4, and FIG. 5). Implant 300 also includes a generally anteriorly positioned bar-like protuberance 420 extending generally superiorly from plate 340. Among other things, protuberance 420 is configured to cooperate with insert 120 to limit the motion of insert 120 relative to plate 340 as discussed further below.

Figure 2:
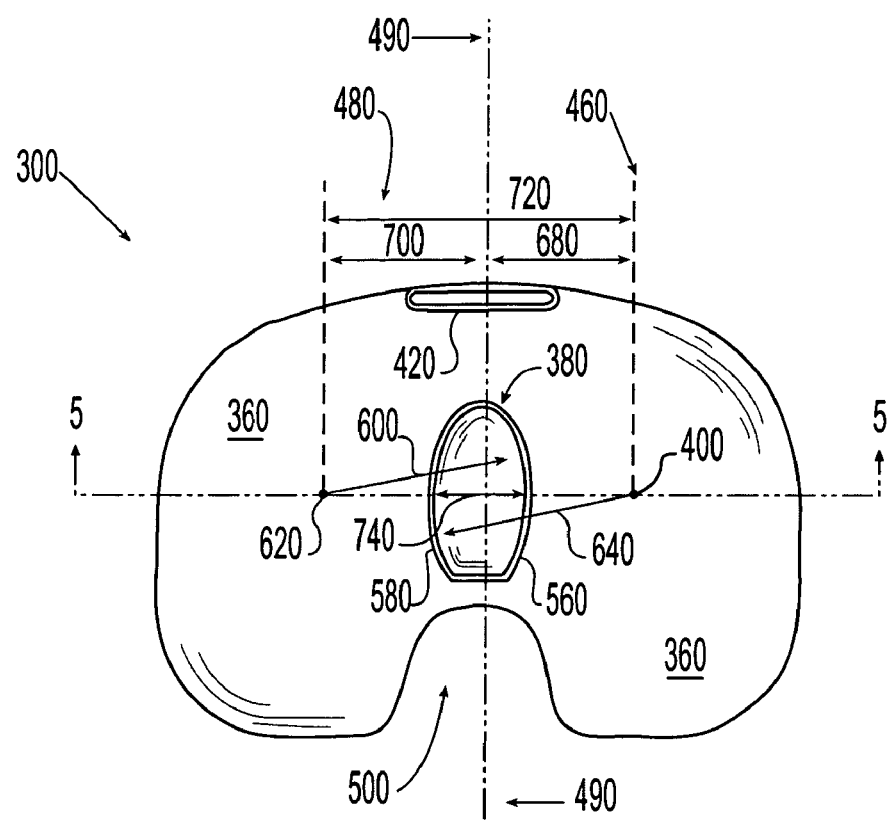
FIG. 2 shows a superior plan view of the exemplary tibial implant of the exemplary sub-assembly of FIG. 1.

FIG. 2 shows a superior plan view of implant 300. As discernable in FIG. 2: plate 340 includes a medial lobe 460 and a lateral lobe 480 conjoined in a dividing plane 490; surface 360 extends over lobe 460 and lobe 480; lobe 460 and lobe 480 together define a generally posteriorly positioned generally U-shaped space 500; and plane 490 medially-laterally bisects protuberance 380, protuberance 420, and space 500. Further, protuberance 380 includes a protuberance sidewall 520 (see FIG. 3) extending from plate 340 and a boss 540 (see FIG. 3) topping off or capping sidewall 520. Boss 540 (see FIG. 3) includes a medial convex arcuate portion 560 and an opposing lateral convex arcuate portion 580 conjoined in plane 490. Portion 560 is eccentric to portion 580, and boss 540 (see FIG. 3) is greater in span anteriorly-posteriorly than it is medially-laterally such that boss 540 (see FIG. 3) is generally ovularly cross-sectionally shaped. More particularly: portion 560 has a curvature radius 600 relative to a laterally-offset axis 620; portion 580 has a curvature radius 640 relative to axis 400; axis 400 is medially disposed from plane 490 by a distance 680; axis 620 is laterally disposed from plane 490 by a distance 700; axis 400 is disposed from axis 620 by a distance 720 that orthogonally passes through plane 490; axis 400 and axis 620 are roughly equidistant from plane 490; radius 600 is roughly equal in magnitude to radius 640; distance 680 is roughly equal in magnitude to distance 700; and portion 560 and portion 580 define a medial-lateral span 740 roughly equaling the scalar sum of radius 600 and radius 640 minus distance 720.

Figure 3:
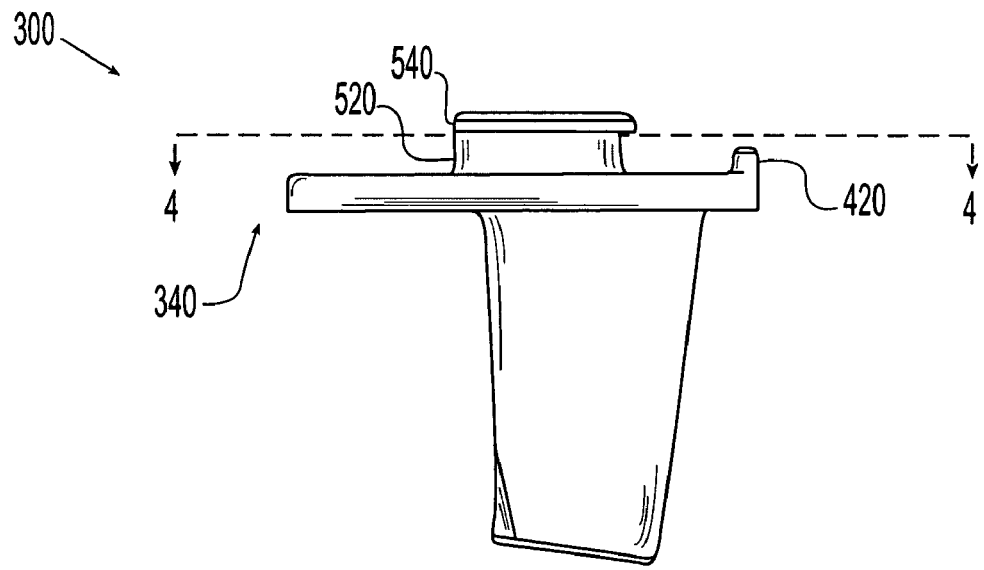
FIG. 3 shows a medial plan view of the exemplary tibial implant of the exemplary sub-assembly of FIG. 1.

FIG. 3 shows a medial plan view of implant 300. Plate 340, protuberance 420, sidewall 520, and boss 540, among other things, are at least partially discernable in FIG. 3.

Figure 4:
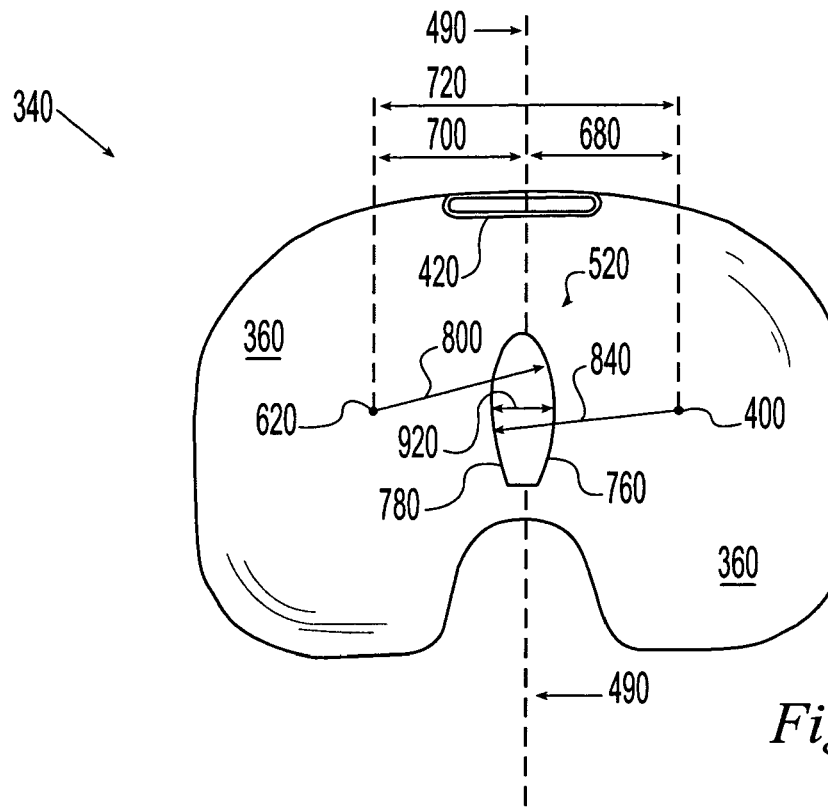
FIG. 4 shows a cross-sectional view of the exemplary tibial implant of the exemplary sub-assembly of FIG. 1 along line 4-4 of FIG. 3.

FIG. 4 shows a cross-sectional view of implant 300 along line 4-4 of FIG. 3. As discernable in FIG. 4: plane 490 medially-laterally bisects sidewall 520; and sidewall 520 includes a medial convex arcuate portion 760 and an opposing lateral convex arcuate portion 780 conjoined in plane 490. Portion 760 is eccentric to portion 780, and sidewall 520 is greater in span anteriorly-posteriorly than it is medially-laterally such that sidewall 520 is generally ovularly cross-sectionally shaped. More particularly: portion 760 has a curvature radius 800 relative to axis 620; portion 780 has a curvature radius 840 relative to axis 400; radius 800 is roughly equal in magnitude to radius 840; and portion 760 and portion 780 define a medial-lateral span 920 roughly equaling the scalar sum of radius 800 and radius 840 minus distance 720. Additionally, radius 800 is somewhat smaller than radius 600 (see FIG. 2) and radius 840 is likewise smaller than radius 640 (see FIG. 2) such that span 740 (see FIG. 2) is somewhat greater than span 920 (see also FIG. 5). Surface 360, protuberance 420, distance 680, and distance 700, among other things, are also at least partially discernable in FIG. 4.

Figure 5:
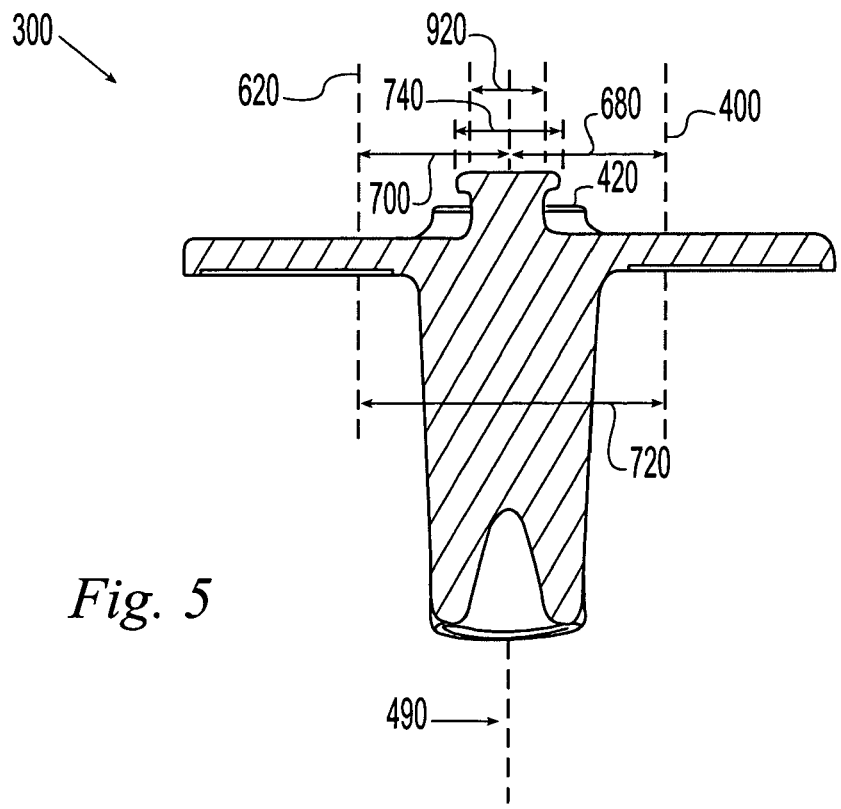
FIG. 5 shows a cross-sectional view of the exemplary tibial implant of the exemplary sub-assembly of FIG. 1 along line 5-5 of FIG. 2.

FIG. 5 shows a cross-sectional view of implant 300 along line 5-5 of FIG. 2. Axis 400, protuberance 420, plane 490, axis 620, distance 680, distance 700, distance 720, distance 740, and distance 920, among other things, are at least partially discernable in FIG. 5.

Figure 6:
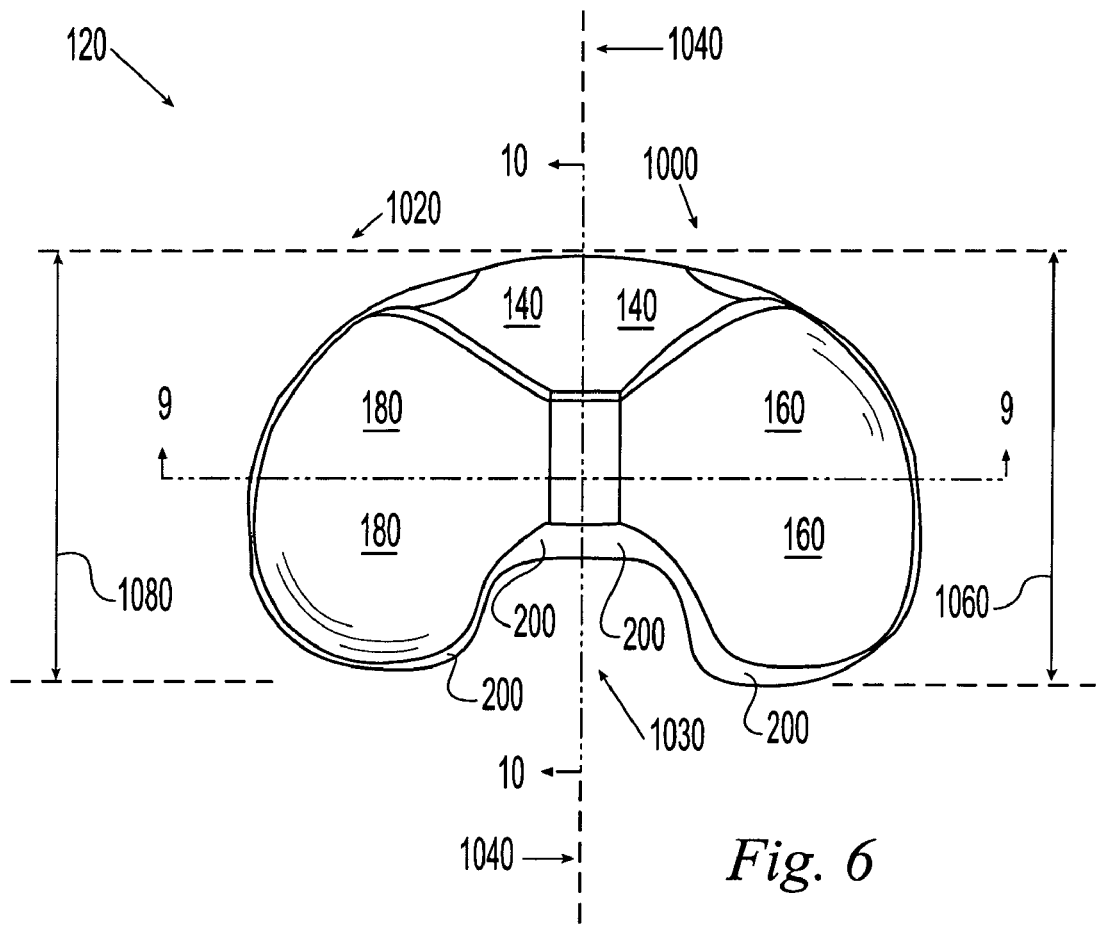
FIG. 6 shows a superior plan view of the exemplary tibio-femoral insert of the exemplary sub-assembly of FIG. 1.

FIG. 6 shows a superior plan view of insert 120. As discernable in FIG. 6, insert 120 includes a medial lobe 1000 and a lateral lobe 1020 conjoined in a dividing plane 1040. Lobe 1000 and lobe 1020 together define a generally posteriorly positioned generally U-shaped space 1030 bisected by plane 1040. Lobe 1000 has anterior-posterior span 1060, while lobe 1020 has anterior-posterior span 1080 that is somewhat smaller than span 1060. In some cases, such anterior-posterior asymmetry may be desirable to enhance modeling of a natural knee (not shown) and/or to otherwise enhance loading/wear characteristics of sub-assembly 100, and/or to reduce the possibility of impingement of the surrounding soft tissues of the knee. However, it is noted that span 1060 and span 1080 may be roughly equal in alternative embodiments. Lobe Surface 140, surface 160, surface 180, and surface 200, among other things, are at least partially discernable in FIG. 6.

Figure 7:
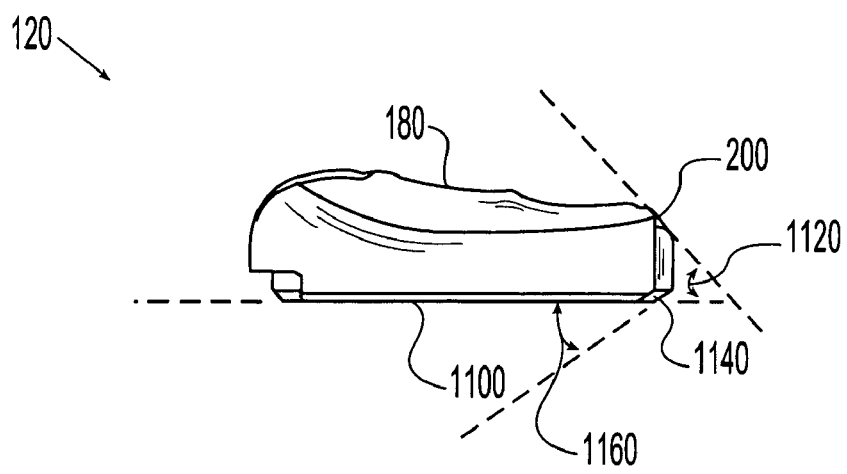
FIG. 7 shows a lateral plan view of the exemplary tibio-femoral insert of the exemplary sub-assembly of FIG. 1.

FIG. 7 shows a lateral plan view of insert 120. As discernable in FIG. 7, insert 120 includes a substantially flat smooth inferior surface 1100 and surface 200 is chamfered at an angle 1120 relative to surface 1100. In the exemplary embodiment, angle 1120 is at least 30 degrees and not more than 65 degrees. Further, lobe 1020 (see FIG. 6) of insert 120 also includes a generally posteriorly positioned chamfered inferior surface 1140 configured to facilitate generally anterior-to-posterior insertion of insert 120 to implant 300 in a minimally invasive operating space (not shown) along line 110 (see FIG. 1). Surface 1140 is chamfered at an angle 1160 relative to surface 1100. Similarly, lobe 1000 (see FIG. 6) also includes a generally posteriorly positioned chamfered inferior surface 1180 (see FIG. 8) configured to facilitate generally anterior-to-posterior insertion of insert 120 to implant 300 in a minimally invasive operating space (not shown) along line 110 (see FIG. 1). Surface 1180 is also chamfered at angle 1160 relative to surface 1100.

Figure 8:
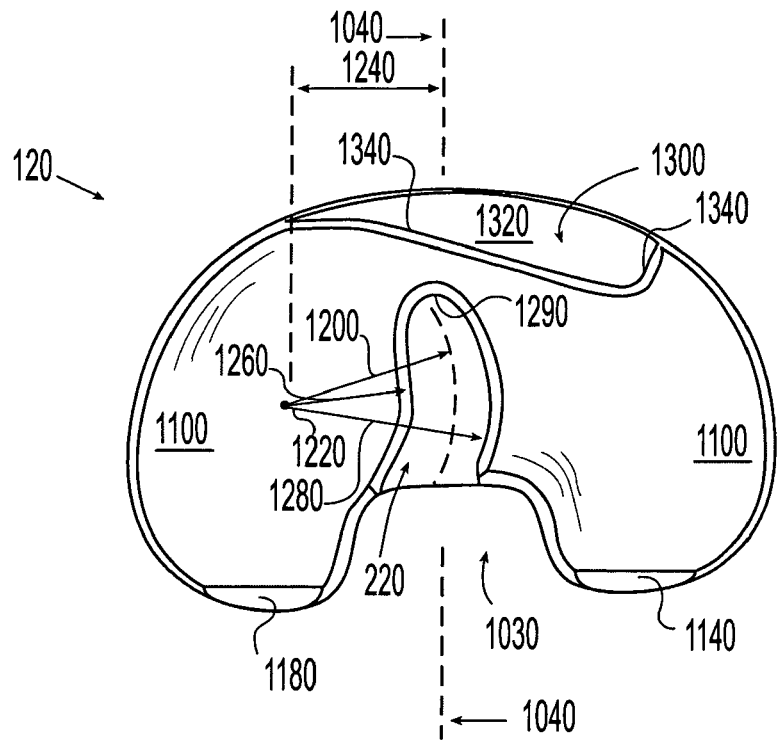
FIG. 8 shows an inferior plan view of the exemplary tibio-femoral insert of the exemplary sub-assembly of FIG. 1.

FIG. 8 shows an inferior plan view of insert 120. As at least partially discernable in FIG. 8, slot 220 opens generally posteriorly and generally inferiorly and extends generally longitudinally into insert 120 with a central or mean curvature radius 1200 relative to an axis 1220. Among other things, slot 220 is configured to receive and slidably engage protuberance 380 (see FIG. 1) such that insert 120 is moveable relative to plate 340 about axis 400 (see FIG. 2, FIG. 4, and FIG. 5) and slot 220 is further configured to inferiorly-superiorly retain boss 540 (see FIG. 3) such that insert 120 is inferiorly-superiorly retained on plate 340. In the exemplary embodiment, slot 220 is arcuately sized to allow about 10-25 degrees of external rotation of insert 120 relative to plate 340 about axis 400. The exemplary embodiment axis 1220 is medially disposed from plane 1040 by a distance 1240, and radius 1200 is roughly equal in magnitude to distance 1240. Distance 1240 is roughly equal in magnitude to distance 680 (see FIG. 4 and FIG. 5). Further, slot 220 has a generally medial-side curvature radius 1260 relative to axis 1220 and a generally lateral-side curvature radius 1280 relative to axis 1220. Radius 1260 is roughly equal in magnitude to distance 720 minus the magnitude of radius 840. Radius 1280 is roughly equal in magnitude to the magnitude of radius 840 (see FIG. 4 and FIG. 8). Slot 220 also includes a roughly innermost portion or apex portion 1290.

As further discernable in FIG. 8, insert 120 also defines a recess 1300 bounded superiorly by a substantially planar smooth ceiling surface 1320 and bounded generally posteriorly and laterally by a wall 1340 that extends generally inferiorly from surface 1320 to surface 1100. In the exemplary embodiment, wall 1340 is configured to prevent any more than about 10-25 degrees of internal rotation of insert 120 relative to plate 340 (see FIG. 1) by abutting against protuberance 420 (see FIG. 1) when the internal rotational limit is reached. Space 1030, surface 1140 and surface 1180, among other things, are also at least partially discernable in FIG. 8.

Figure 9:
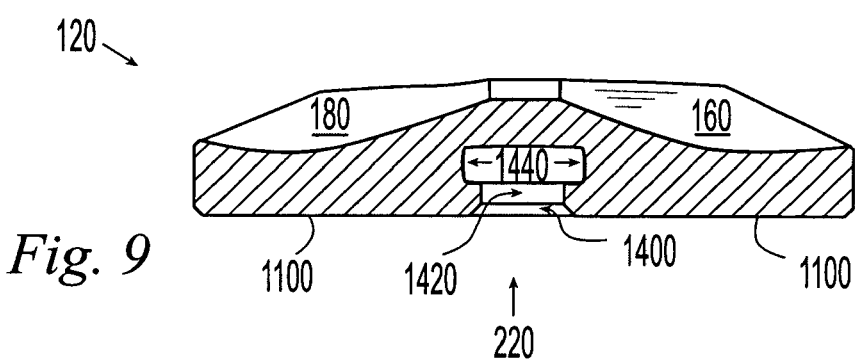
FIG. 9 shows a cross-sectional view of the exemplary tibio-femoral insert of the exemplary sub-assembly of FIG. 1 along line 9-9 of FIG. 6.

FIG. 9 shows a cross-sectional view of insert 120 along line 9-9 of FIG. 6. As at least partially discernable in FIG. 9, slot 220 includes a tapered portion 1400 opening at surface 1100, extending generally superiorly from surface 1100, and arcing generally posteriorly-anteriorly inward. Further, slot 220 includes a neck portion 1420 extending generally superiorly from portion 1400 and arcing generally posteriorly-anteriorly inward. Portion 1420 is configured to slidably engage portion 520 of protuberance 380 (see FIG. 3). Slot 220 also includes a head portion 1440 extending generally superiorly from portion 1420 and arcing generally posteriorly-anteriorly inward. Portion 1440 is configured to inferior-superiorly retain boss 540 (see FIG. 3) without significantly interfering with the slidable engagement between portion 1420 of slot 220 and portion 520 of protuberance 380. Surface 160 and surface 180, among other things, are also at least partially discernable in FIG. 9.

Figure 10:
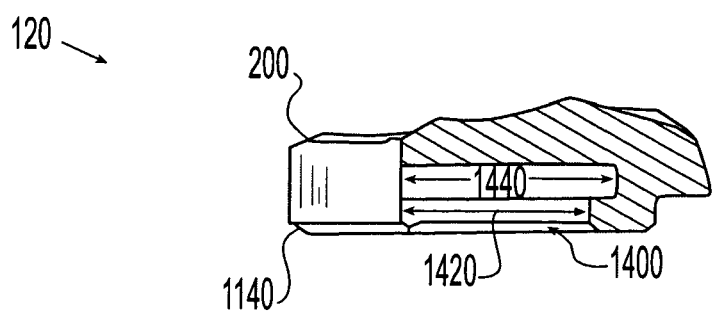
FIG. 10 shows a cross-sectional view of the exemplary tibio-femoral insert of the exemplary sub-assembly of FIG. 1 along line 10-10 of FIG. 6.

FIG. 10 shows a cross-sectional view of insert 120 along line 10-10 of FIG. 6. Surface 200, surface 1140, portion 1400, portion 1420, and portion 1440, among other things, are at least partially discernable in FIG. 10.

Figure 11:
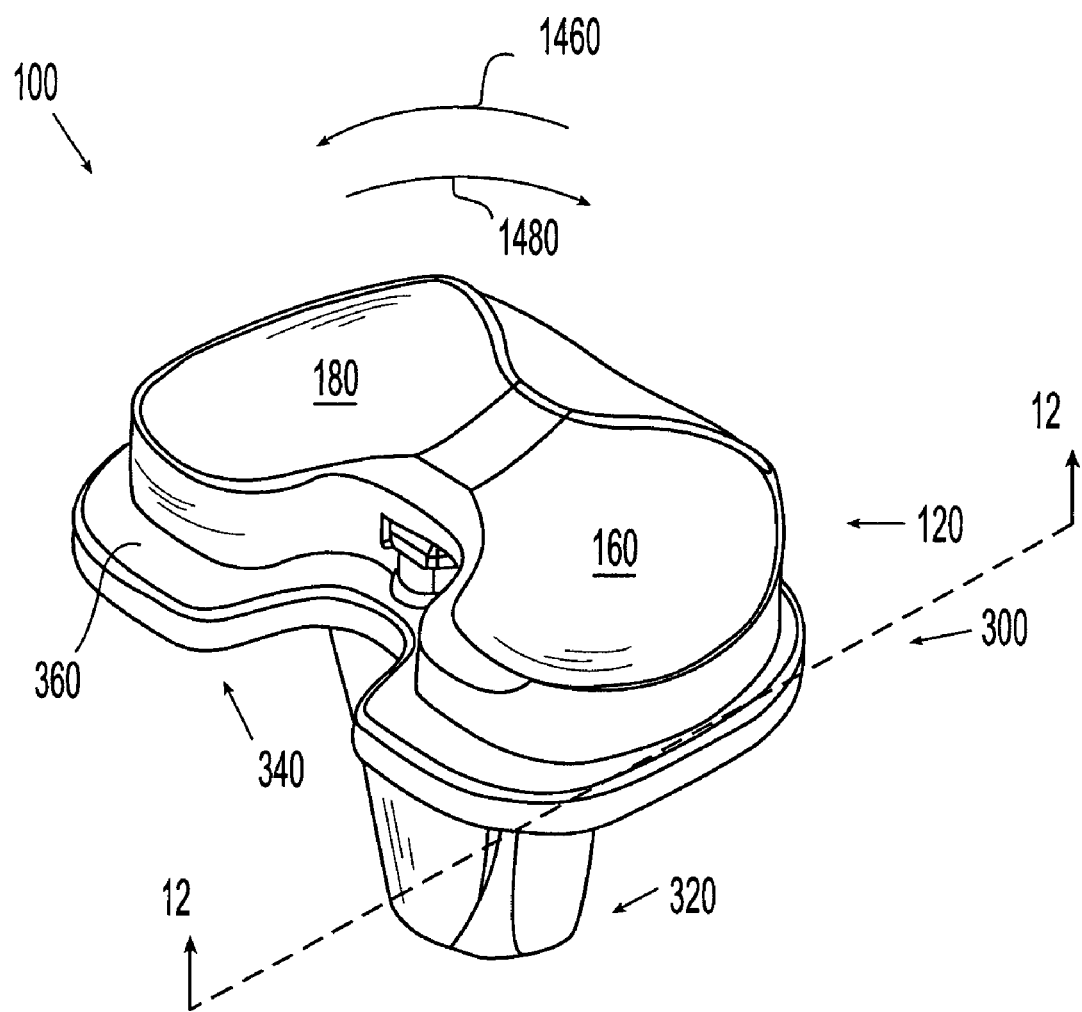
FIG. 11 shows an assembled perspective view of the exemplary sub-assembly of FIG. 1.

FIG. 11 shows an assembled perspective view of sub-assembly 100. Insert 120 (including surface 160 and surface 180) and implant 300 (including stem 320, plate 340, and surface 360 of plate 340), among other things, are at least partially discernable in FIG. 11. In assembly of sub-assembly 100, a surgeon or other user suitably opens a knee joint in a known manner. After properly resecting the affected proximal tibia, the user anchors stem 320 of implant 300 into the proximal tibia as known. After anchoring implant 300, the user positions insert 120 generally anteriorly to and slightly superiorly to plate 340 (see FIG. 1), and tips insert 120 to generally align it with line 110 (see FIG. 1). It is noted that in FIG. 1 the superior positioning of insert 120 and the sloping of line 110 are exaggerated for clarity of exposition. To complete the assembly, the user progressively slides slot 220 over protuberance 380 (moving insert 120 generally anteriorly to posteriorly into the joint space) until protuberance 420 clears wall 1340 such that insert 120 snaps into final engagement with tibial plate 340. It should be appreciated that this low-profile, generally anterior to posterior assembly is well suited for minimally invasive surgeries. After insert 120 is snapped into engagement with plate 340, the user attaches a suitable femoral implant to the distal femur and closes the surgical site as known. An alternate embodiment of the disclosed invention includes a removable anterior protuberance to facilitate insertion of tibio-femoral insert 120 to implant 300.

Figure 12:
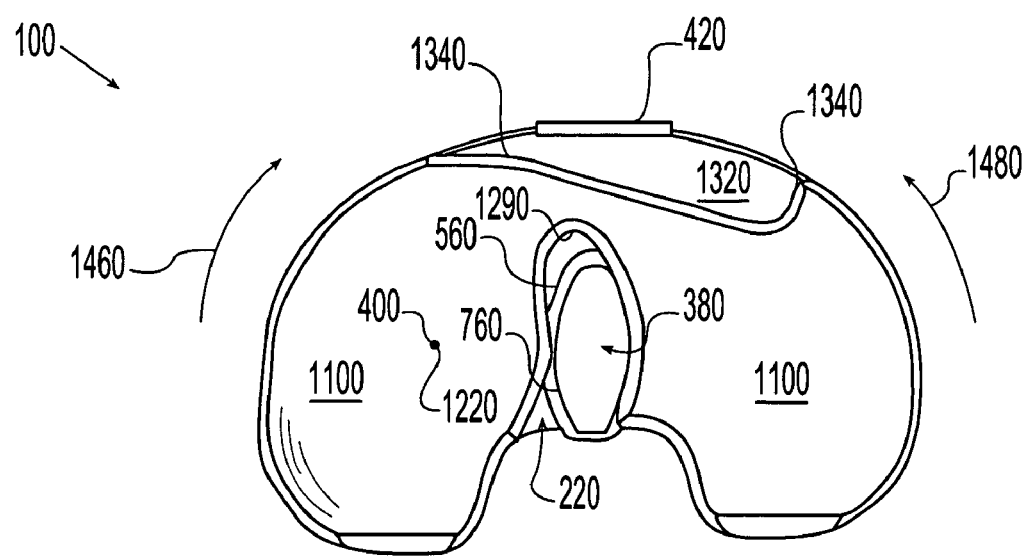
FIG. 12 shows a cross-sectional view of the exemplary sub-assembly of FIG. 1 along line 12-12 of FIG. 11.

FIG. 12 shows a cross-sectional view of sub-assembly 100 along line 12-12 of FIG. 11. In operation of exemplary sub-assembly 100, axis 1220 (insert 120) remains roughly axially aligned with axis 400 (implant 300), surface 360 (implant 300; see FIG. 1) slidably supports surface 1100 (insert 120), and the slidable engagement between protuberance 380 (implant 300) and slot 220 (insert 120) provides freedom of motion (more particularly, external rotational freedom) for insert 120 relative to plate 340 about axis 400 (and axis 1220) as generally indicated by directional line 1460. The external rotational freedom is limited to about 10-25 degrees when protuberance 380 abuts portion 1290 of slot 220. The engagement between protuberance 380 and slot 220 also provides internal rotational freedom for insert 120 relative to plate 340 about axis 400 (and axis 1220) as generally indicated by directional line 1480. However, the internal rotational freedom is not limited by protuberance 380 or slot 220. The internal rotational freedom of insert 120 relative to plate 340 is limited to about 10-25 degrees when protuberance 420 abuts wall 1340. Further, it is noted that the elongated arcuate engagement between portion 780 (protuberance 380; see FIG. 4) and slot 220 with the roughly equal curvature radii increases contact surface area between insert 120 and protuberance 380 and, thus, provides more resistance to axial micro-motion and anterior-posterior shear forces. Portion 560, portion 760, and surface 1320, among other things, are at least partially discernable in FIG. 12.

Figure 13:
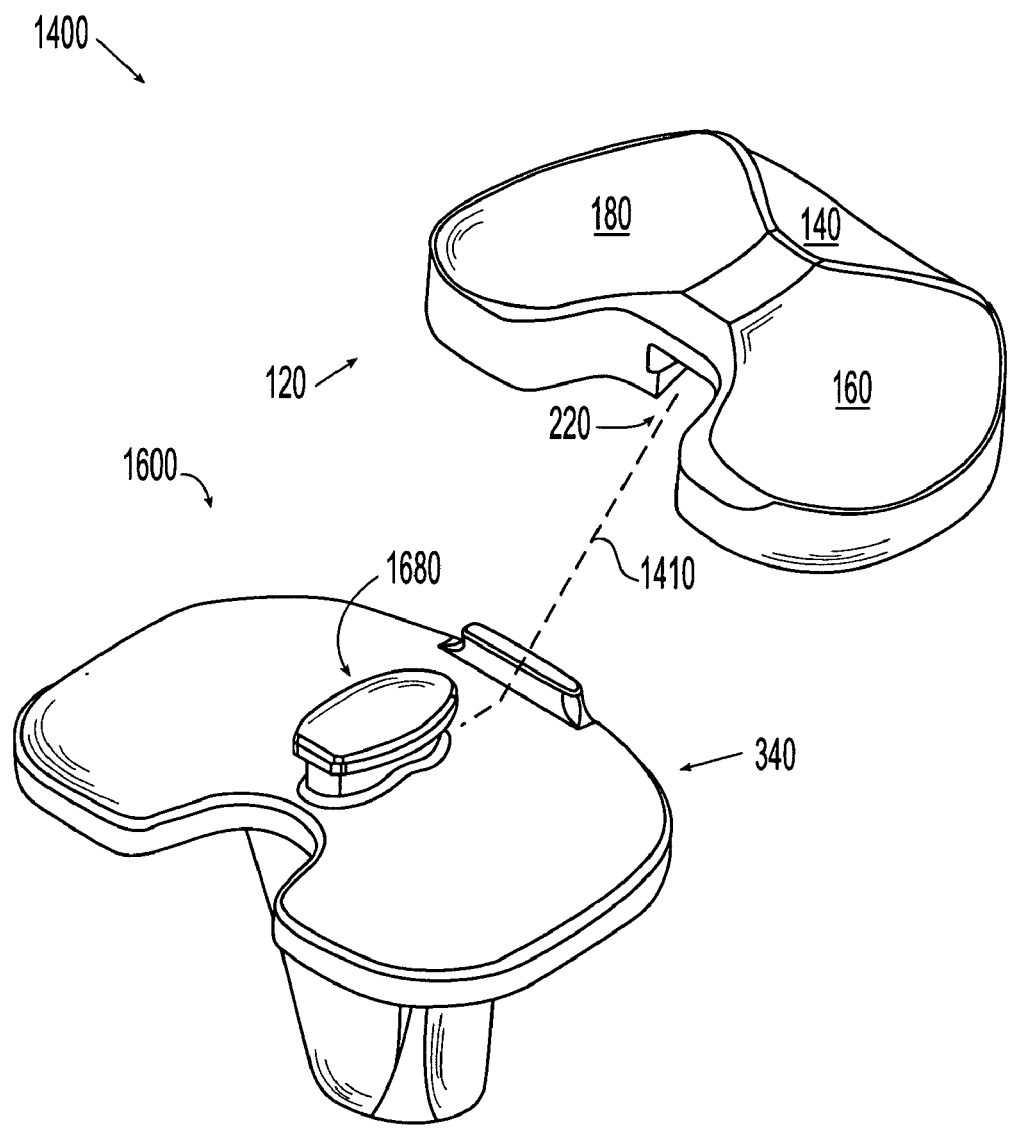
FIG. 13 shows an exploded perspective view of an exemplary alternative mobile bearing knee prosthesis sub-assembly according to the present invention along an explosion/assembly line.

FIG. 13 shows an exploded perspective view of an exemplary alternative mobile bearing knee prosthesis sub-assembly 1400 according to the present invention along an explosion/assembly line 1410. Sub-assembly 1400 includes insert 120 (discussed above) and an alternative tibial implant 1600. Implant 1600 is identical to implant 300 (discussed above) with the exception that protuberance 380 is replaced with an alternative generally centrally positioned stud-like protuberance 1680 extending generally superiorly from plate 340.

Figure 14:
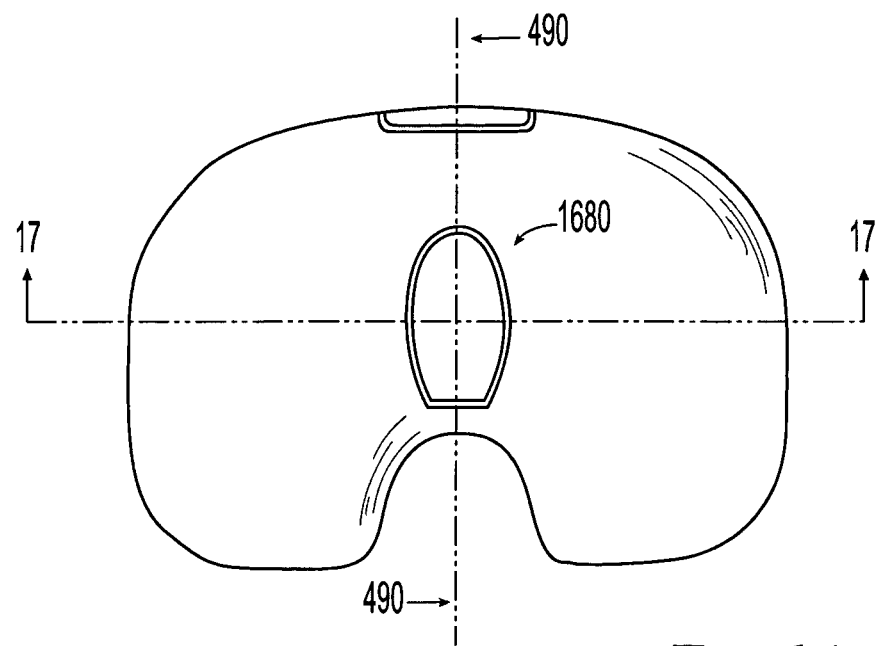
FIG. 14 shows a superior plan view of the exemplary tibial implant of the exemplary sub-assembly of FIG. 13.

FIG. 14 shows a superior plan view of implant 1600. As discernable in FIG. 14, plane 490 medially-laterally bisects protuberance 1680.

Figure 15:
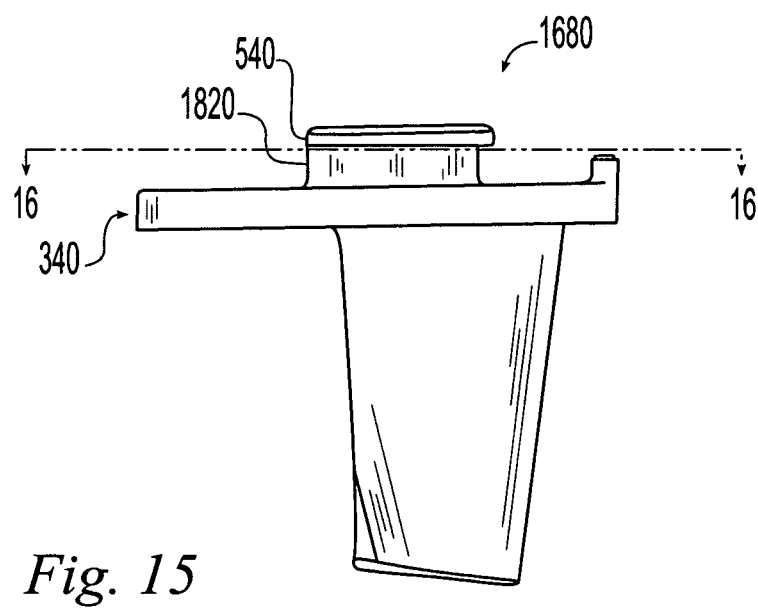
FIG. 15 shows a medial plan view of the exemplary tibial implant of the exemplary sub-assembly of FIG. 13.

FIG. 15 shows a medial plan view of implant 1600. Protuberance 1680 is identical to protuberance 380 with the exception that protuberance sidewall 520 is replaced with an alternative protuberance sidewall 1820 extending from plate 340 to boss 540.

Figure 16:
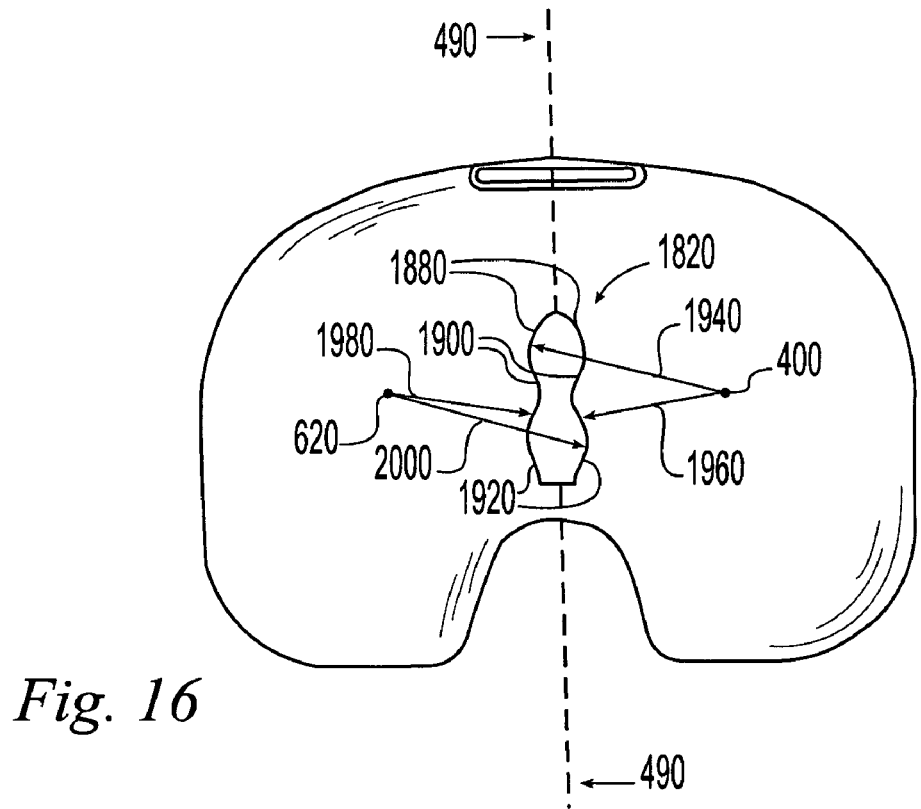
FIG. 16 shows a cross-sectional view of the exemplary tibial implant of the exemplary sub-assembly of FIG. 13 along line 16-16 of FIG. 15.

FIG. 16 shows a cross-sectional view of implant 1600 along line 16-16 of FIG. 15. As discernable in FIG. 16: plane 490 medially-laterally bisects sidewall 1820; and sidewall 1820 includes a generally anteriorly positioned pair of opposing convex arcuate portions 1880, a generally centrally positioned pair of opposing concave arcuate portions 1900, and a generally posteriorly positioned pair of opposing convex arcuate portions 1920. Portions 1880 have opposing curvature radii 1940 relative to axis 400 and axis 620, respectively (for clarity of depiction, only the radius relative to axis 400 is shown). Radii 1940 are equal in magnitude to radius 800 (discussed above). Portions 1900 have opposing curvature radii 1960 and 1980 relative to axis 400 and axis 620, respectively. Radii 1960 and 1980 are equal in magnitude to radius 1260 (discussed above). Portions 1920 have opposing curvature radii 2000 relative to axis 400 and axis 620, respectively (for clarity of depiction, only the radius relative to axis 620 is shown). Radii 2000 are equal in magnitude to radius 800 (discussed above). Consequently, it should be appreciated that in the exemplary embodiment protuberance 1680 is generally hour-glass cross-sectionally shaped.

Figure 17:
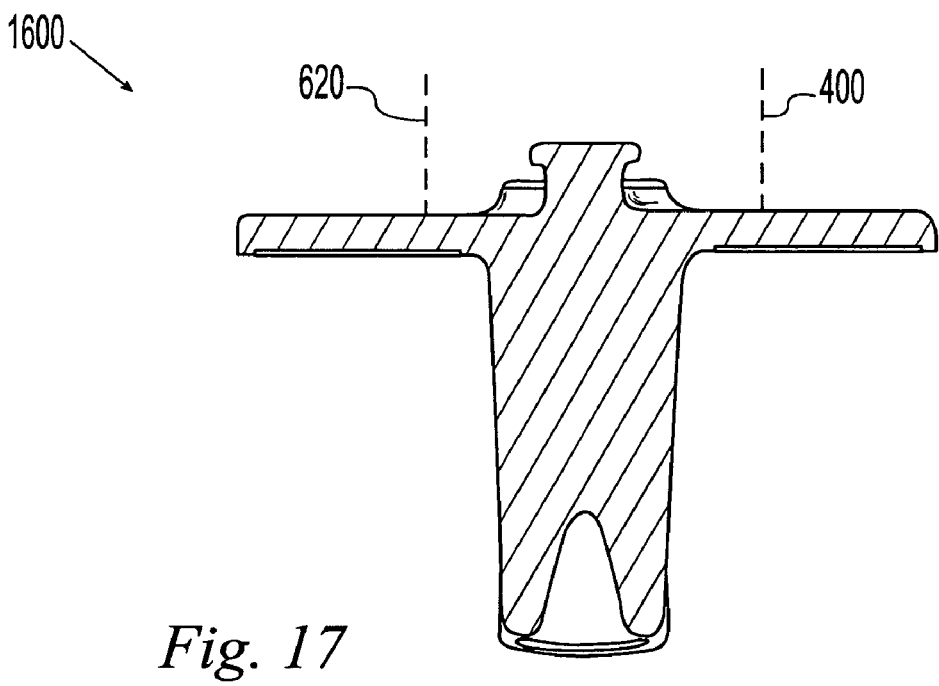
FIG. 17 shows a cross-sectional view of the exemplary tibial implant of the exemplary sub-assembly of FIG. 13 along line 17-17 of FIG. 14.

FIG. 17 shows a cross-sectional view of implant 1600 along line 17-17 of FIG. 14. Axis 400 and axis 620, among other things, are at least partially discernable in FIG. 17.

Figure 18:
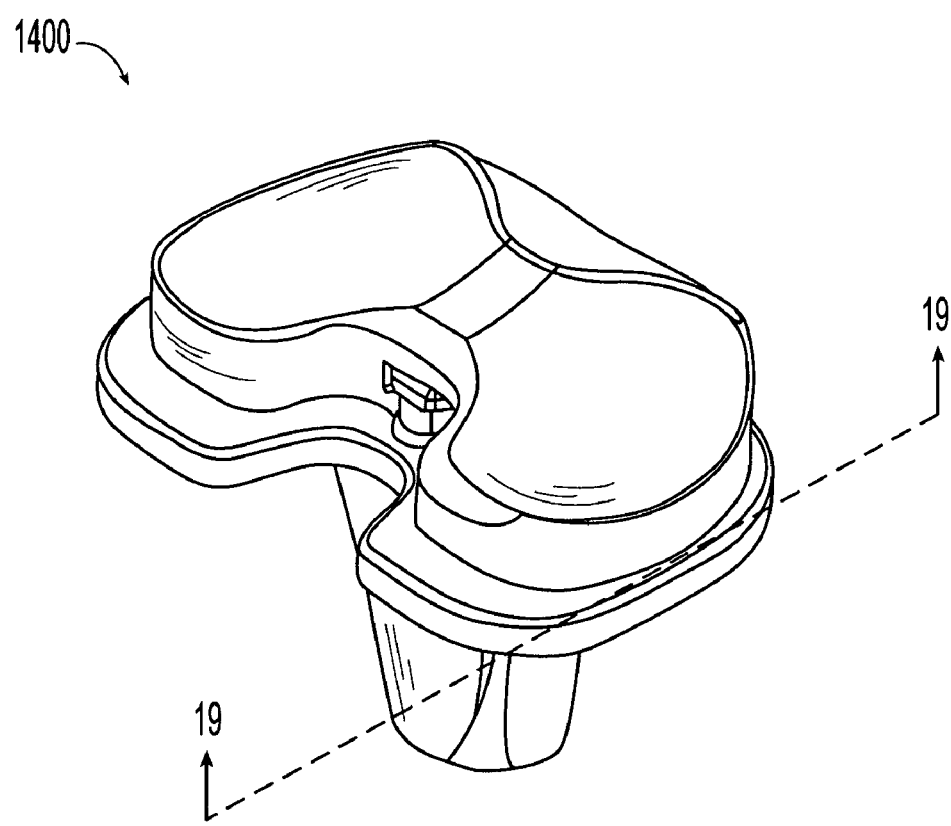
FIG. 18 shows an assembled perspective view of the exemplary sub-assembly of FIG. 13.
Figure 19:
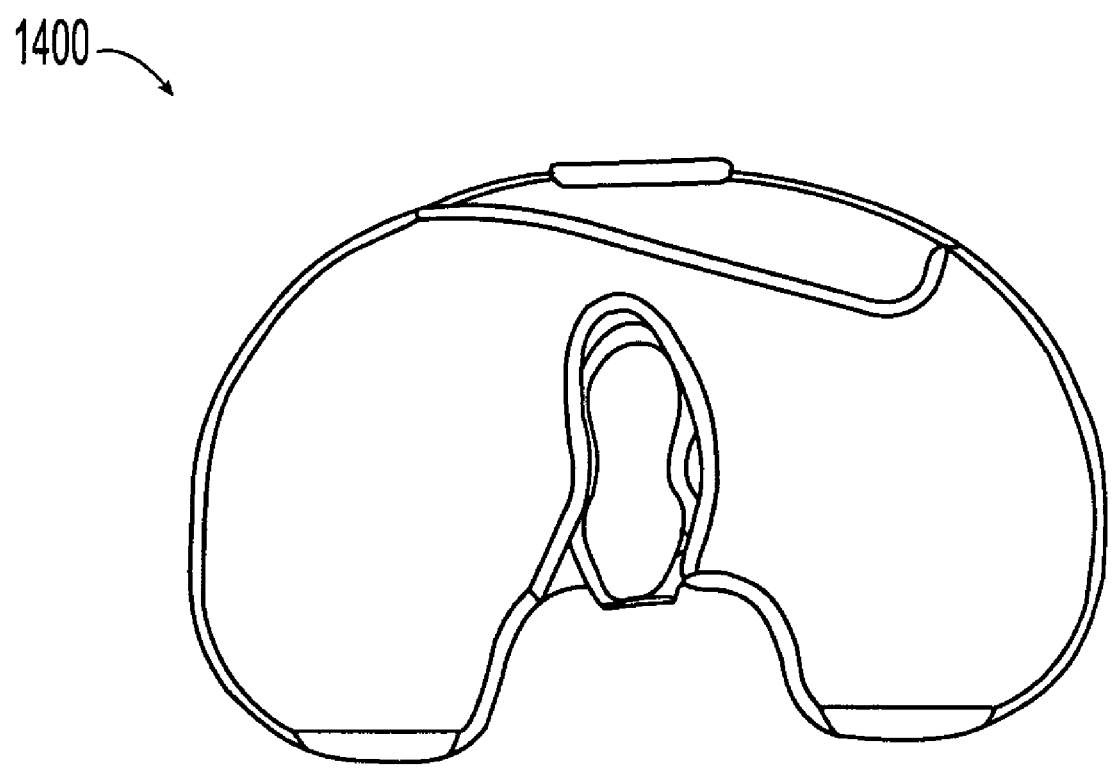
FIG. 19 shows a cross-sectional view of the exemplary sub-assembly of FIG. 13 along line 19-19 of FIG. 18.
Figure 20:
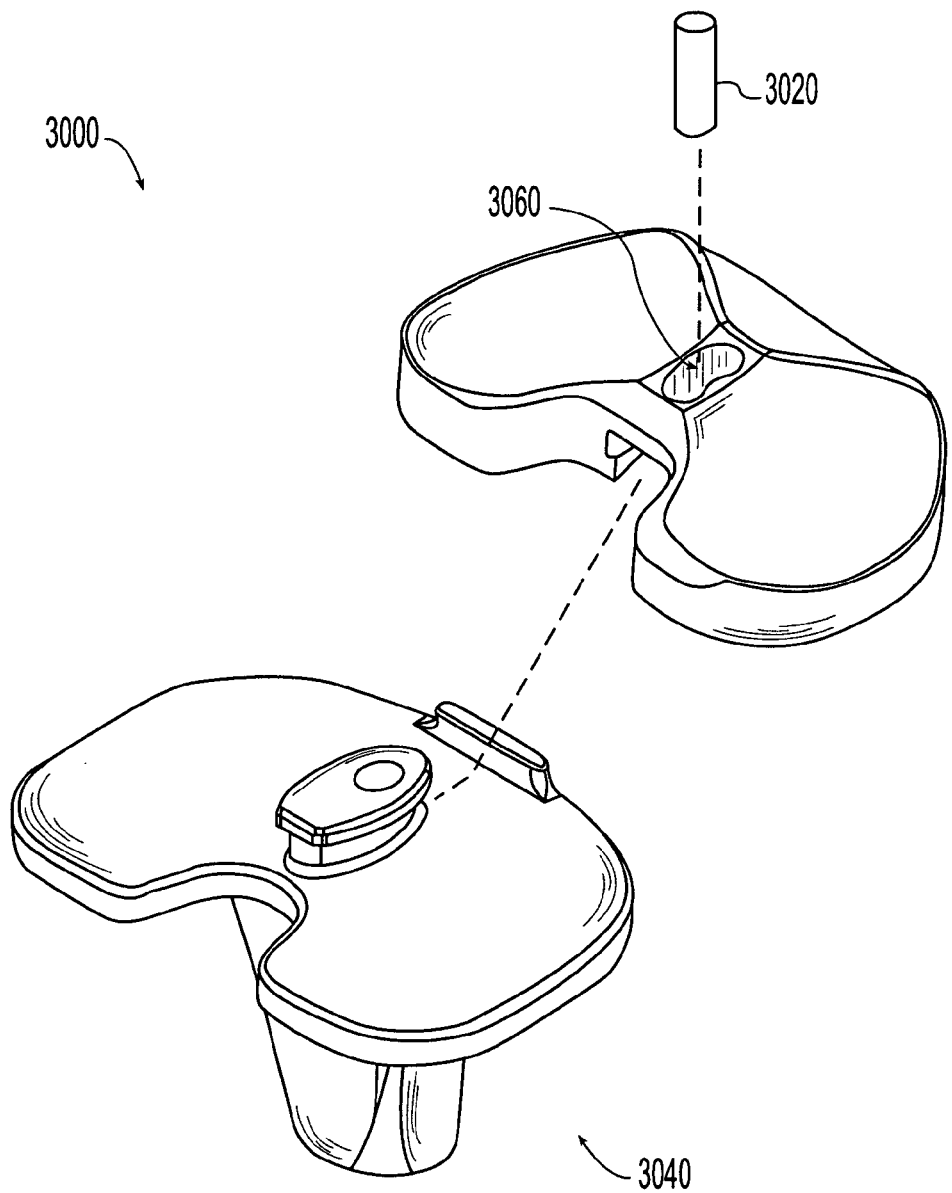
FIGS. 20-30 show views of another exemplary alternative mobile bearing knee prosthesis sub-assembly according to the present invention.
Figure 21:
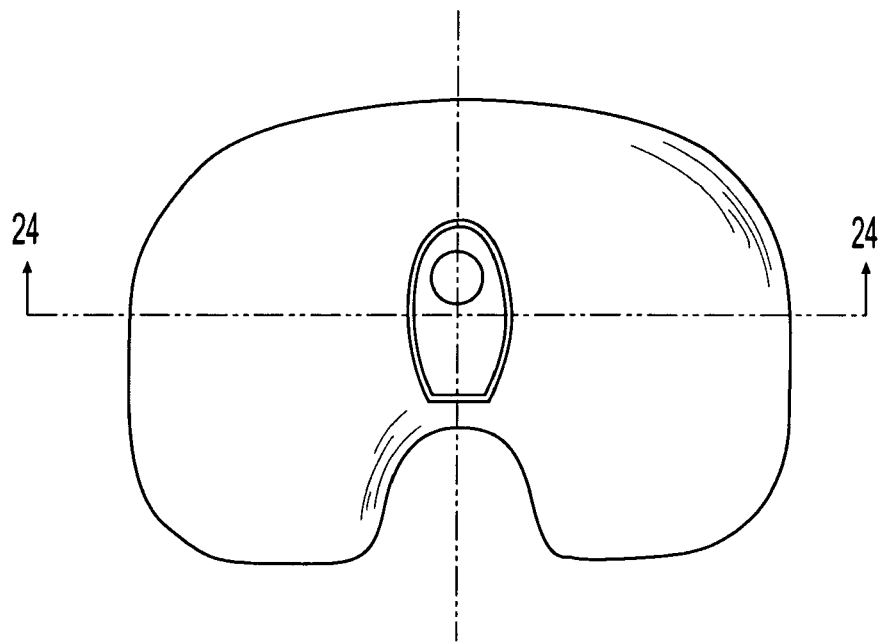
Figure 22:
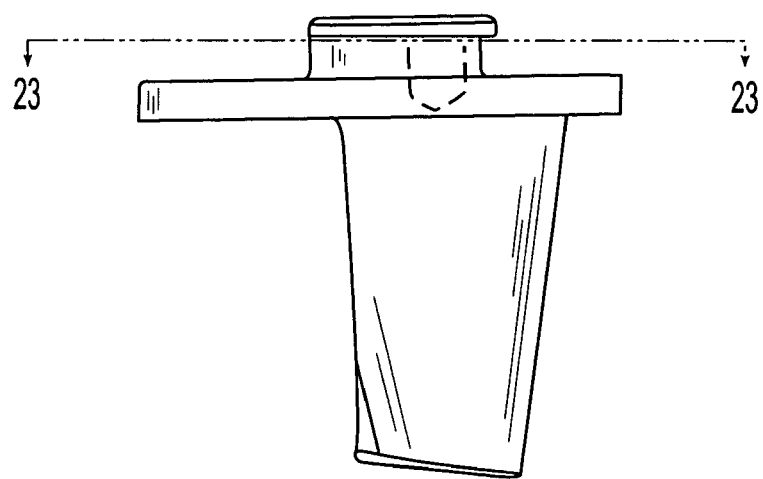
Figure 23:
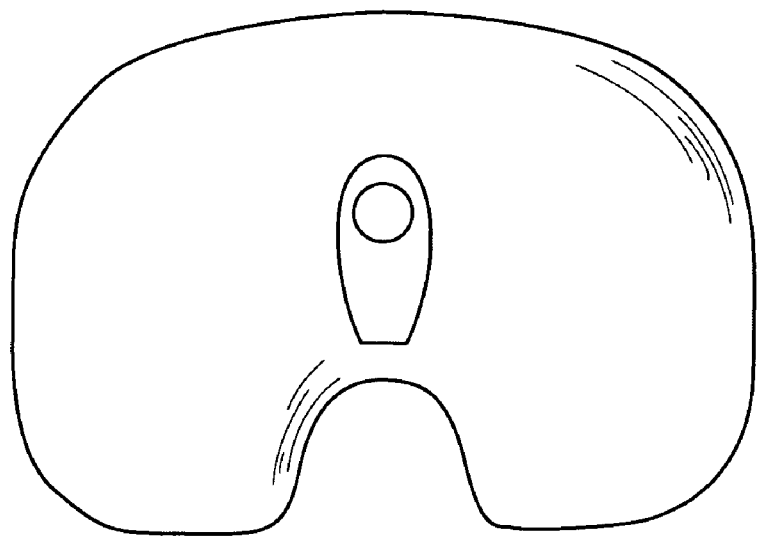
Figure 24:
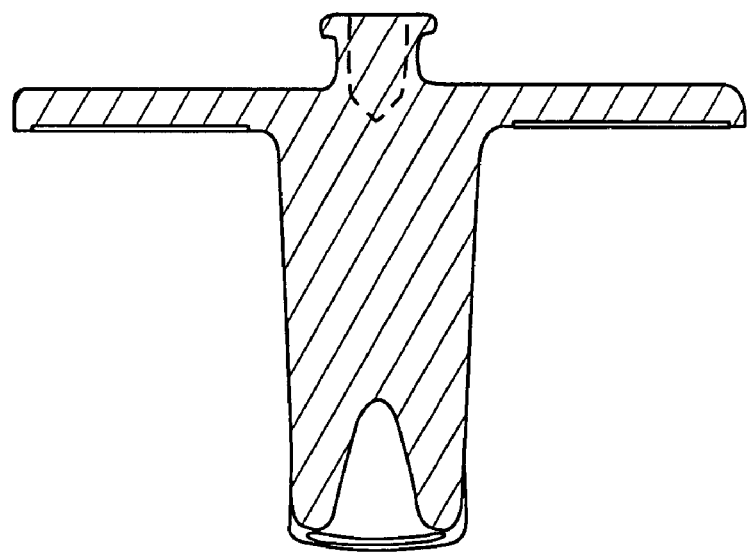
Figure 25:
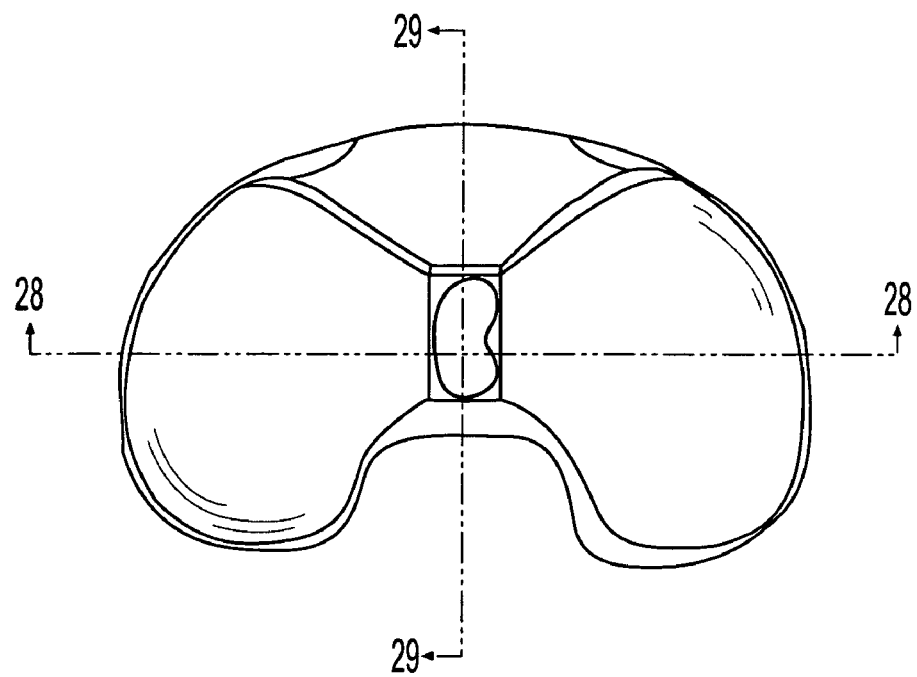
Figure 26:
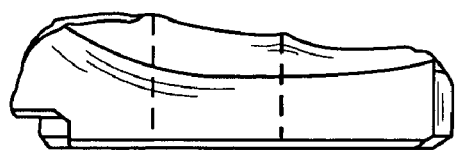
Figure 27:
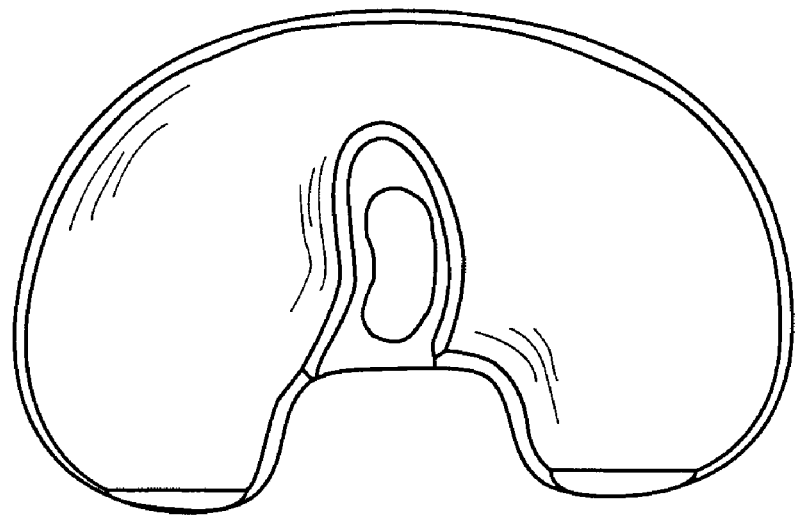
Figure 28:
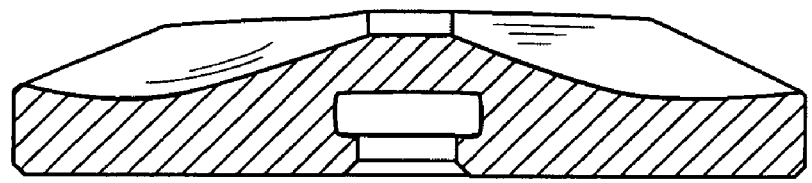
Figure 29:
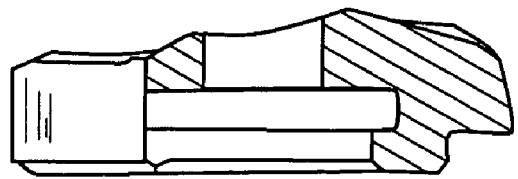
Figure 30:
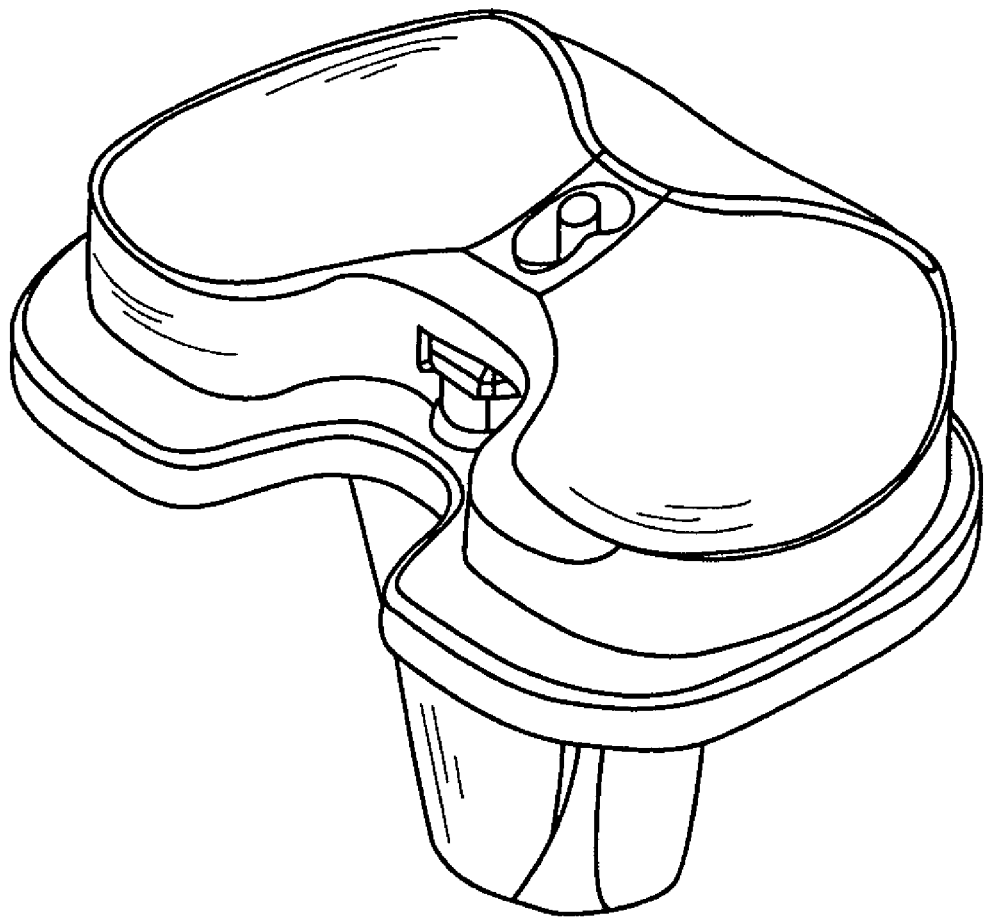
Figure 31:
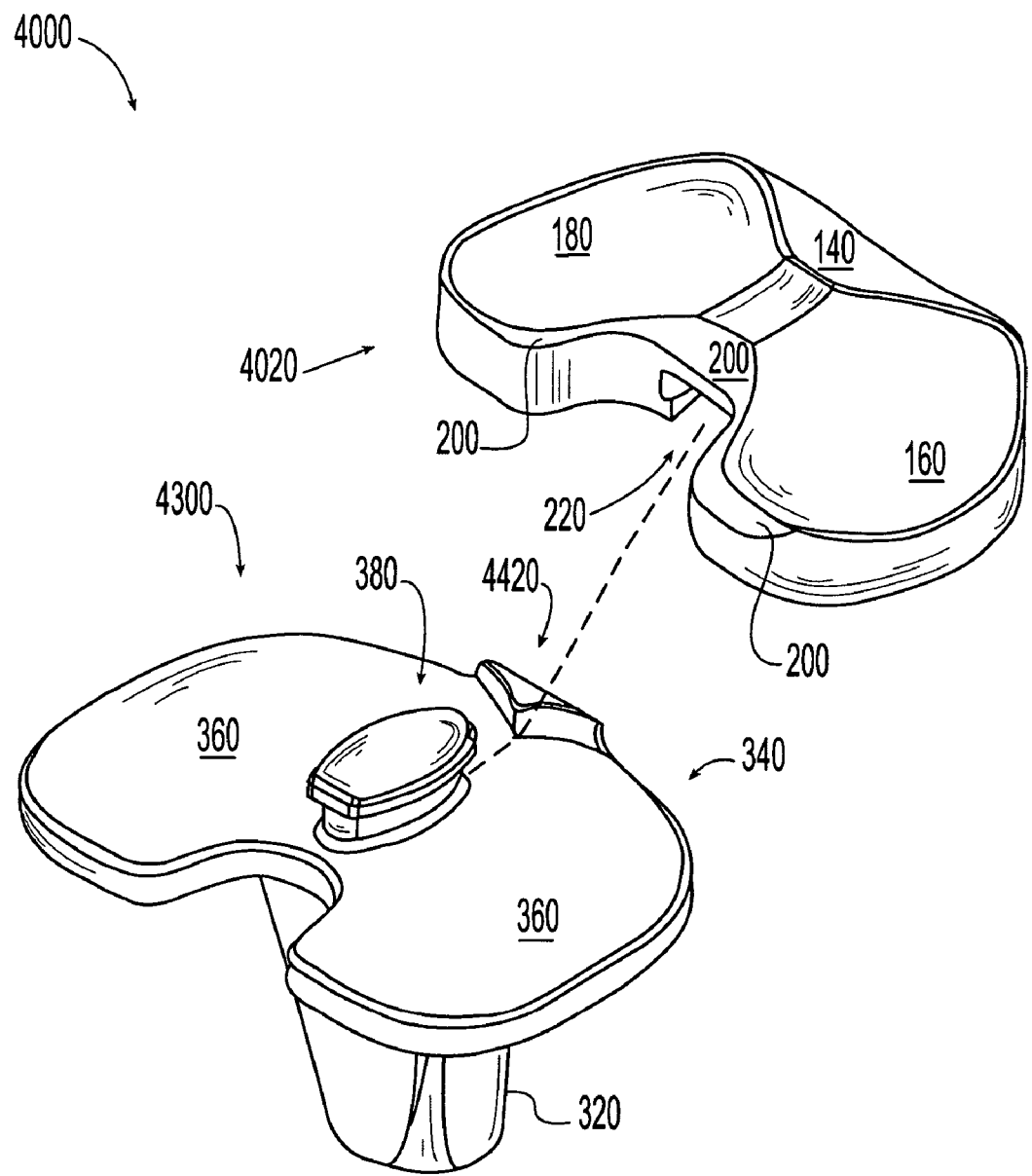
FIGS. 31-42 show views of another exemplary alternative mobile bearing knee prosthesis sub-assembly according to the present invention.
Figure 32:
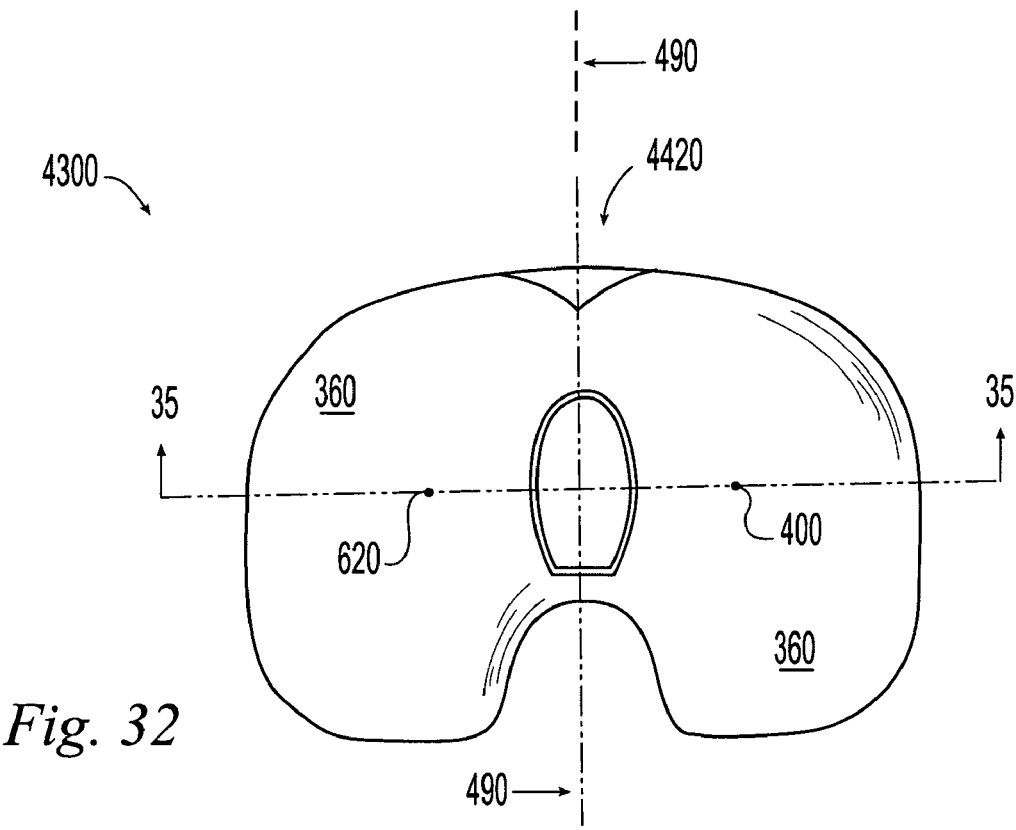
Figure 33:
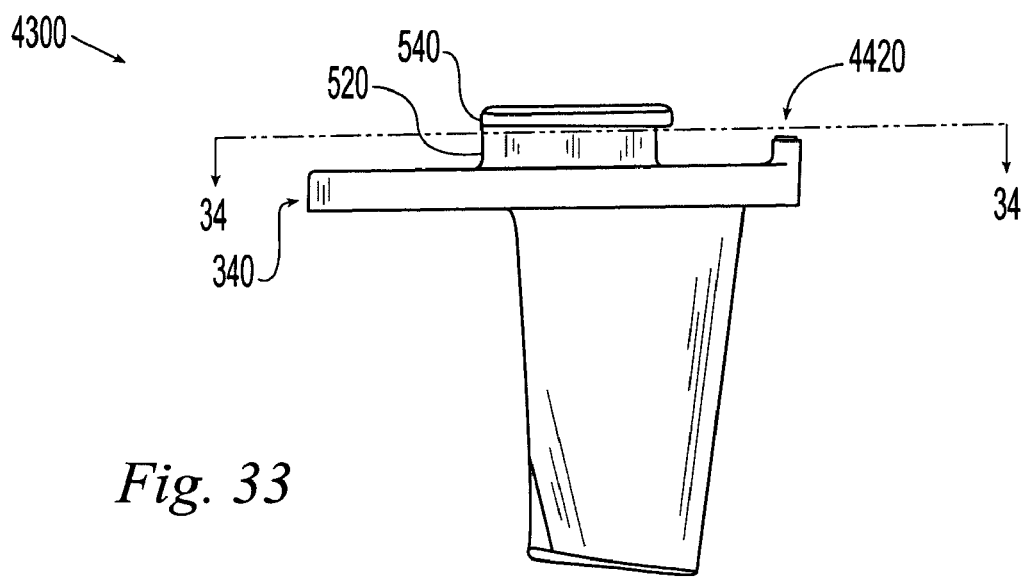
Figure 34:
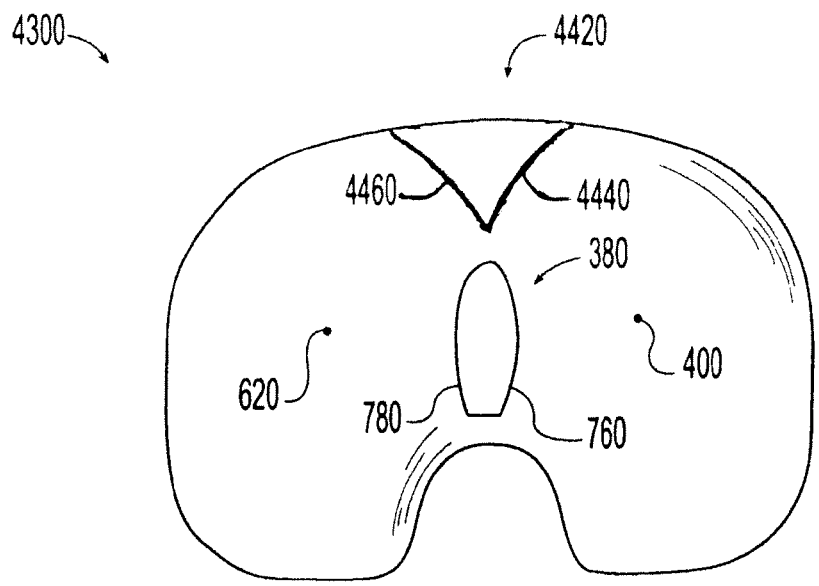
Figure 35:
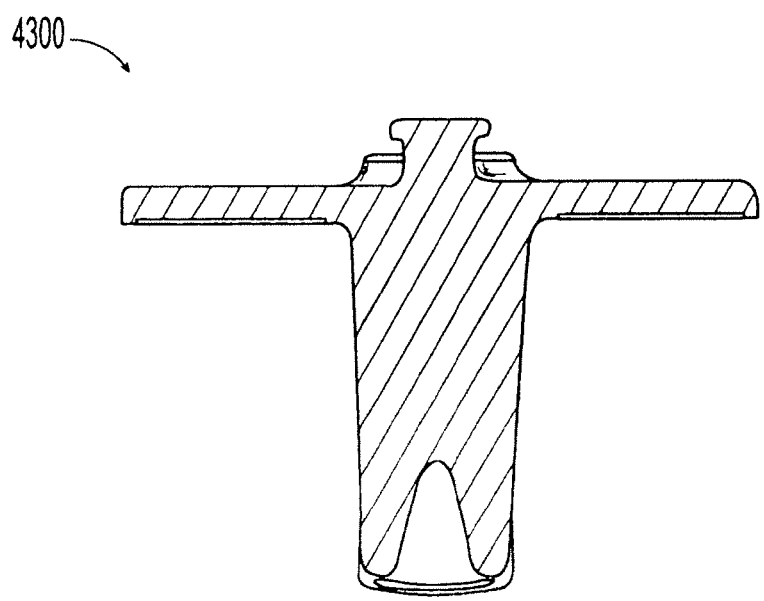
Figure 36:
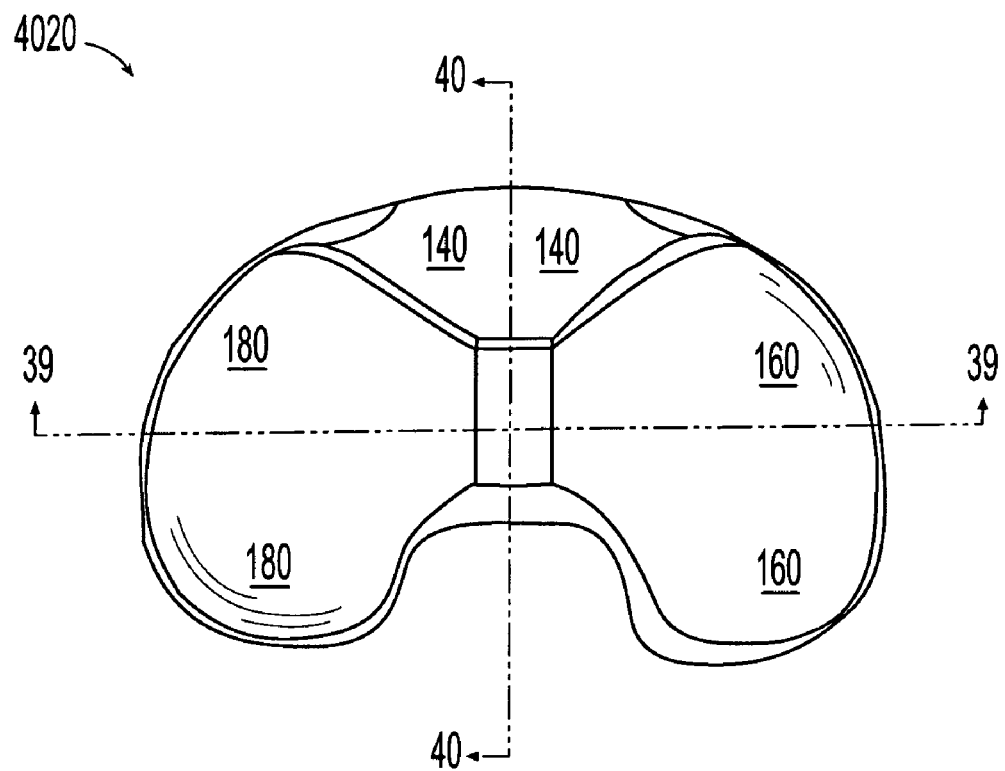
Figure 37:
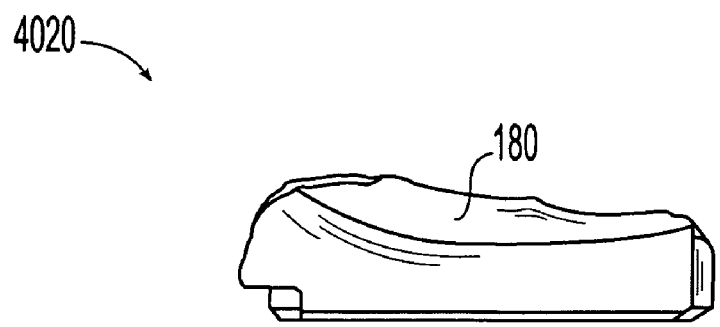
Figure 38:
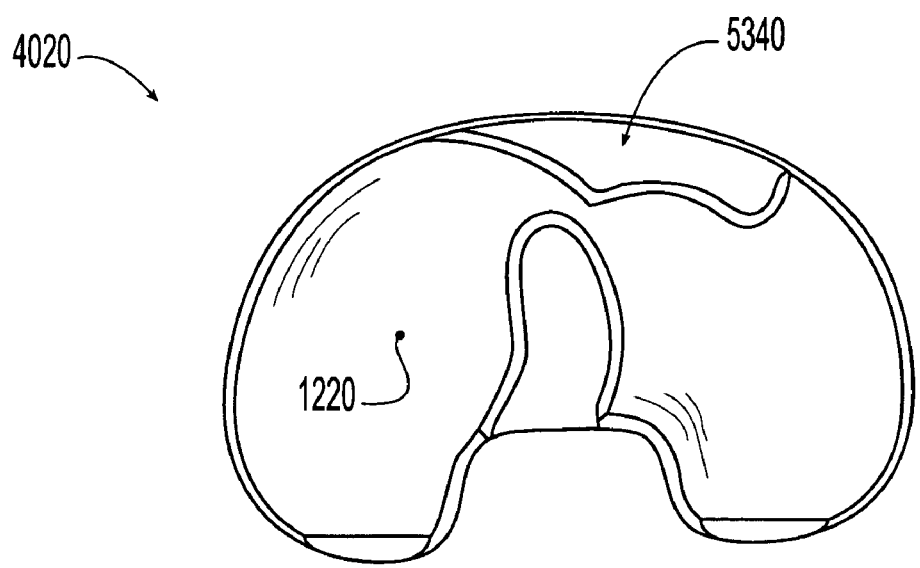
Figure 39:
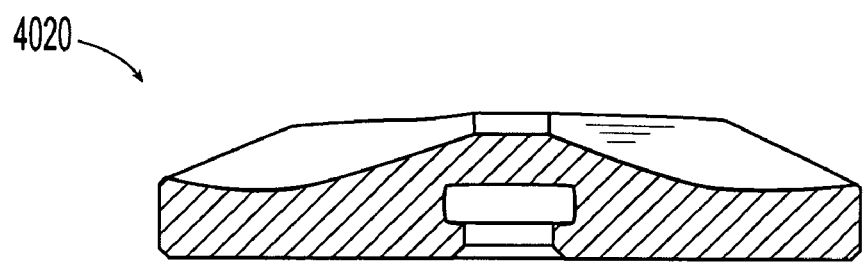
Figure 40:
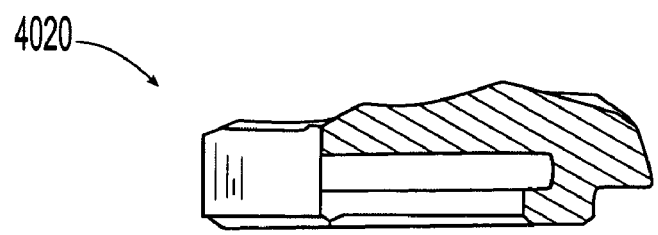
Figure 41:
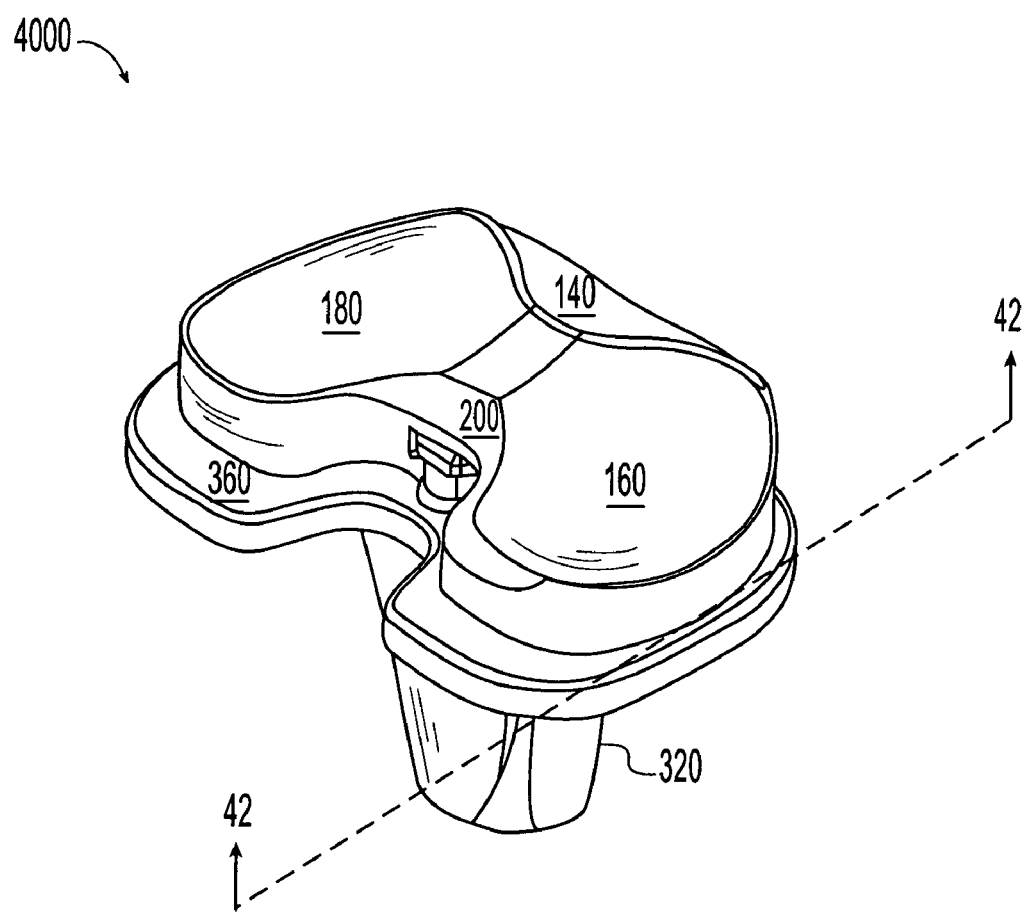
Figure 42:
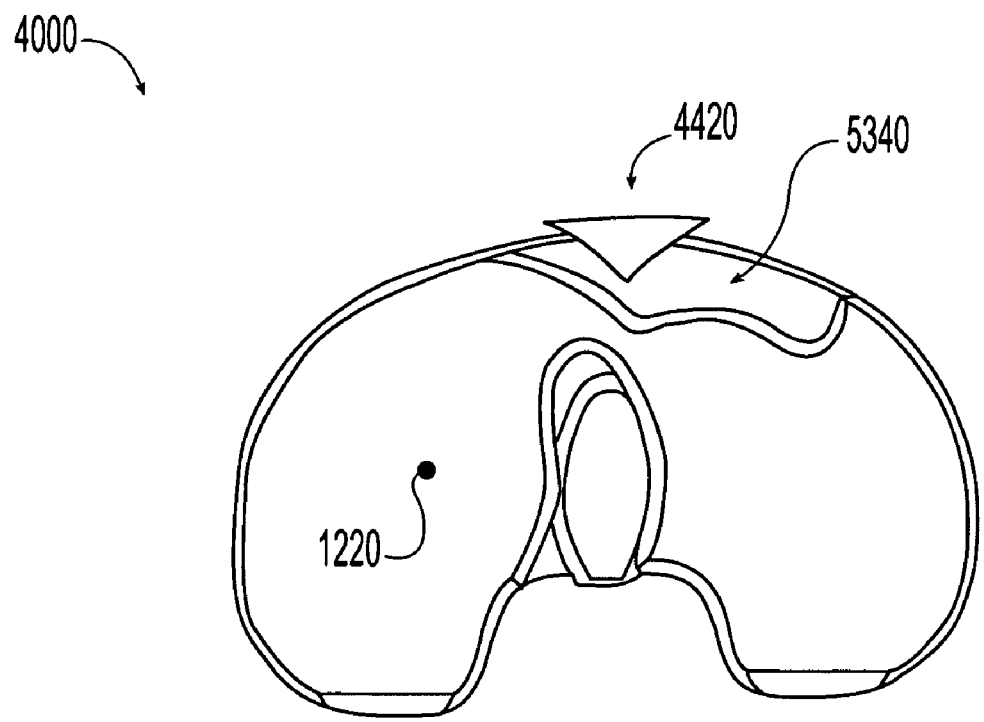

FIG. 18 shows an assembled perspective view of sub-assembly 1400; and FIG. 19 shows a cross-sectional view of sub-assembly 1400 along line 19-19 of FIG. 18. Assembly and operation of sub-assembly 1400 should be readily appreciable from the drawings and from reference to the assembly and operation of sub-assembly 100 (discussed above).

FIGS. 20-30 show views of another exemplary alternative mobile bearing knee prosthesis sub-assembly 3000 according to the present invention. Sub-assembly 3000 is made and used in a like manner to sub-assembly 100 with the notable exceptions that protuberance 420 (see FIG. 1) and wall 1340 (see FIG. 8) are omitted, and internal/external rotational stop features are provided by a generally centrally positioned peg 3020 or, alternatively, a screw extending generally superiorly from an alternative tibial implant 3040 in cooperation with an arcuate inferiorly and posteriorly open channel 3060 into which peg 3020 protrudes. Assembly and operation of sub-assembly 3000 should be readily appreciable from the drawings and from reference to the assembly and operation of sub-assembly 100 (discussed above).

FIGS. 31-42 show views of another exemplary alternative mobile bearing knee prosthesis sub-assembly 4000 according to the present invention. Sub-assembly 4000 is made and used in a like manner to sub-assembly 100 with the notable exceptions that internal/external rotational stop features are provided by cooperation between an alternative bi-arcuate protuberance 4420 (see FIG. 31) and an alternative wall 5340 (see FIG. 38) that replace protuberance 420 (see FIG. 1) and wall 1340 (see FIG. 8), respectively. Further, it is noted that protuberance 4420 includes a generally medially positioned arcuate surface 4440 that is concentric to portion 780 of protuberance 340, and includes a generally laterally positioned arcuate surface 4460 that is concentric to portion 760 of protuberance 380 (see FIG. 34). Assembly and operation of sub-assembly 4000 should be readily appreciable from the drawings and from reference to the assembly and operation of sub-assembly 100 (discussed above).

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A mobile bearing knee prosthesis apparatus, comprising:
    a tibial plate including a medial lobe and a lateral lobe conjoined in a dividing plane;
    a protuberance extending from the tibial plate, the protuberance including a protuberance sidewall, the protuberance sidewall being bisected by the dividing plane and including a pair of opposing eccentric convex arcuate portions, the pair of opposing eccentric convex arcuate portions including a first convex arcuate portion having a curvature radius relative to an axis medially offset from the dividing plane and a second convex arcuate portion having a curvature radius relative to an axis laterally offset from the dividing plane; and
    a tibio femoral insert defining a slot having a generally lateral-side curvature radius roughly equal to the curvature radius of the first convex arcuate portion of the protuberance sidewall and a generally medial-side curvature radius, a lateral-side curvature radius origin defined by said lateral-side curvature radius medially offset from the dividing plane, a medial-side curvature radius origin defined by said medial side curvature radius medially offset from the dividing plane;
    wherein the tibio-femoral insert is rotatable relative to the tibial plate about the medially offset axis when the protuberance sidewall is positioned in the slot.

2. The apparatus of claim 1, wherein the medially offset axis is disposed from the dividing plane by a first distance, and the slot has a mean curvature radius roughly equal in magnitude to the first distance.

3. The apparatus of claim 2, wherein the generally medial-side curvature radius is roughly equal to a distance between the laterally offset axis and the medially offset axis minus the curvature radius of the first convex arcuate portion of the protuberance sidewall.

4. The apparatus of claim 3, wherein the protuberance sidewall is generally ovularly cross-sectionally shaped.

5. The apparatus of claim 1, wherein the protuberance sidewall further includes a pair of opposing eccentric concave arcuate portions, the pair of opposing eccentric concave arcuate portions includes a first concave arcuate portion having a curvature radius relative to the medially offset axis, the pair of opposing eccentric concave arcuate portions further includes a second concave arcuate portion having a curvature radius relative to the laterally disposed axis, and the curvature radius of the first concave arcuate portion is roughly equal in magnitude to the curvature radius of the second concave arcuate portion.

6. The apparatus of claim 5, wherein the medially offset axis is disposed from the dividing plane by a first distance, and the slot has a mean curvature radius roughly equal in magnitude to the first distance.

7. The apparatus of claim 6, wherein the medial-side curvature radius is roughly equal to a distance between the laterally offset axis and the medially offset axis minus the curvature radius of the first convex arcuate portion of the protuberance sidewall.

8. The apparatus of claim 7, wherein the protuberance sidewall is generally hour-glass cross-sectionally shaped.

9. The apparatus of claim 1, further comprising:
    a bar extending from the tibial plate;
    wherein the tibio-femoral insert defines a recess and the bar is positioned in the recess.

10. The apparatus of claim 9, wherein the bar is removable from the tibial plate.

11. The apparatus of claim 9, wherein the bar is bisected by the dividing plane and includes a plurality of arcuate surfaces.

12. The apparatus of claim 1, further comprising:
    a bar extending from the tibial plate;
    wherein the bar includes a generally medially positioned arcuate surface concentric to the first convex arcuate portion of the protuberance sidewall of the protuberance, the bar further includes a generally laterally positioned arcuate surface concentric to the second convex arcuate portion of the protuberance sidewall of the protuberance, the tibio-femoral insert defines a recess, and the bar is positioned in the recess.

13. The apparatus of claim 1, further comprising:
    a peg extending from the protuberance; and
    wherein the tibio-femoral insert defines a second, arcuate slot and the peg extends into the second, arcuate slot.

14. The apparatus of claim 1, further comprising:
    a screw extending from the protuberance; and
    wherein the tibio-femoral insert defines a second, arcuate slot and the screw extends into the second, arcuate slot.

15. The apparatus of claim 1, wherein the protuberance extending from the tibial plate has a medial-lateral span roughly equaling the scalar sum of the curvature radius of the first convex arcuate portion and the curvature radius of the second convex arcuate portion minus the distance between the centers of the curvature radius of the first convex arcuate portion and the curvature radius of the second convex arcuate portion.

16. A tibial prosthesis, comprising:
a tibial component comprising:
a proximal surface; and
a protuberance extending superiorly from said proximal surface of said tibial component, said protuberance bisected by an anterior-posterior dividing plane, said protuberance having a first convex sidewall extending superiorly from said proximal surface of said tibial component and facing outwardly from said dividing plane, said protuberance having a second convex sidewall extending superiorly from said proximal surface of said tibial component and facing outwardly from said dividing plane, said dividing plane defining a first side of said proximal surface and a second side of said proximal surface, said first convex sidewall facing said first side of said proximal surface and having a convex curvature defined by a first radius having a center offset from the dividing plane in a direction toward the second side of the proximal surface, said second convex sidewall facing said second side of said proximal surface and having a convex curvature defined by a second radius having a center offset from the dividing plane in a direction toward the first side of the proximal surface;
a first tibio-femoral insert defining a slot sized to receive said protuberance of said tibial component, said slot defined by a wall having a first curvature radius and a second curvature radius, a first curvature radius origin defined by said first curvature radius medially offset from the dividing plane, a second curvature radius origin defined by said second curvature radius medially offset from the dividing plane, said first curvature radius and said second curvature radius sized and oriented to cooperate with said first convex sidewall of said protuberance to guide rotation of said first tibio-femoral insert about a first axis parallel to said dividing plane and intersecting said center of said first radius.

17. The tibial prosthesis of claim 16, further comprising:
a second tibio-femoral insert defining a second slot sized to receive said protuberance of said tibial component, said second slot defined by a second wall having a curvature radius sized and oriented to cooperate with said second convex sidewall of said protuberance to guide rotation of said second tibio-femoral insert about a second axis parallel to said dividing plane and intersecting said center of said second radius.

18. The tibial prosthesis of claim 16, wherein the first radius is offset from the dividing plane by a first distance, and the slot has a mean curvature radius roughly equal in magnitude to the first distance.

19. The tibial prosthesis of claim 16, wherein the first convex sidewall and the second convex sidewall together form at least a part of a protuberance sidewall that is generally ovularly cross-sectionally shaped.

20. The tibial prosthesis of claim 16, wherein the first convex sidewall and the second convex sidewall together form at least a part of a protuberance sidewall that is generally hour-glass cross-sectionally shaped.

21. The tibial prosthesis of claim 16, further comprising:
a bar extending from the tibial component;
wherein the first tibio-femoral insert defines a recess and the bar is positioned in the recess.

22. The tibial prosthesis of claim 21, wherein the bar is bisected by the dividing plane and includes a plurality of arcuate surfaces.

23. The tibial prosthesis of claim 16, further comprising:
a peg extending from the protuberance; and
wherein the first tibio-femoral insert defines a second, arcuate slot and the peg extends into the second, arcuate slot.

24. A mobile bearing knee prosthesis apparatus, comprising:
a tibial plate including a medial lobe and a lateral lobe conjoined in a dividing plane;
a protuberance extending from the tibial plane, the protuberance including a protuberance sidewall, the protuberance sidewall bisected by the dividing plane and including a pair of opposing eccentric convex arcuate portions, the pair of opposing eccentric convex arcuate portions including a first convex arcuate portion having a curvature radius relative to an axis medially offset from the dividing plane and a second convex arcuate portion having a curvature radius relative to an axis laterally offset from the dividing plane; and
a tibio-femoral insert defining a slot having a generally lateral-side curvature radius roughly equal to the curvature radius of the first convex arcuate portion of the protuberance sidewall and a generally medial-side curvature radius, a lateral-side curvature radius origin defined by said lateral-side curvature radius medially offset from the dividing plane, a medial-side curvature radius origin defined by said medial-side curvature radius medially offset from the dividing plane, said slot sized to receive the protuberance extending from the tibial plate and to allow an external rotation of the tibio-femoral insert relative to the tibial plate when the protuberance extending from the tibial plate is positioned in the slot of the tibio-femoral insert, the external rotation allowed by cooperation of the slot and protuberance being in a range of 10-25°.

* * * * *